United States Patent
Heinze et al.

(10) Patent No.: US 11,066,485 B2
(45) Date of Patent: Jul. 20, 2021

(54) MODIFIED STARCH

(71) Applicant: Corn Products Development, Inc., Westchester, NJ (US)

(72) Inventors: Friedrich Heinze, Bridgewater, NJ (US); Justus Hierneis, Bridgewater, NJ (US)

(73) Assignee: Corn Products Development, Inc., Westchester, IL (US)

( * ) Notice: Subject to any disclaimer, the term of this patent is extended or adjusted under 35 U.S.C. 154(b) by 0 days.

(21) Appl. No.: 16/628,552

(22) PCT Filed: Jul. 9, 2018

(86) PCT No.: PCT/US2018/041283
§ 371 (c)(1),
(2) Date: Jan. 3, 2020

(87) PCT Pub. No.: WO2019/014121
PCT Pub. Date: Jan. 17, 2019

(65) Prior Publication Data
US 2020/0216572 A1    Jul. 9, 2020

(30) Foreign Application Priority Data

Jul. 10, 2017   (EP) .................................. 17180478

(51) Int. Cl.
*C08B 31/04* (2006.01)
*A61K 9/50* (2006.01)
*B01J 13/06* (2006.01)

(52) U.S. Cl.
CPC ............ *C08B 31/04* (2013.01); *A61K 9/5036* (2013.01); *A61K 9/5089* (2013.01); *B01J 13/06* (2013.01)

(58) Field of Classification Search
CPC ...... C08B 31/04; A61K 9/5036; A61K 9/5089
See application file for complete search history.

(56) References Cited

U.S. PATENT DOCUMENTS 5,185,176 A  *  2/1993  Chiu ................... B01F 17/0021
                                                        426/590

FOREIGN PATENT DOCUMENTS

EP        0 332 027 A1    2/1989
EP        1 484 055 A1    6/2004

* cited by examiner

*Primary Examiner* — Pancham Bakshi
(74) *Attorney, Agent, or Firm* — Rachael Casey

(57) ABSTRACT

Described herein is an octenyl succinic acid modified starch (OSA modified starch) degraded by at least one enzyme capable of cleaving 1,4-linkages of a starch molecule from the non-reducing ends to produce short chain saccharides, wherein the content of non-covalently bound, free octenyl succinic acid in the OSA modified starch is less than about 0.50% by weight, based on total weight of the modified starch, and wherein content of alpha-1,6-glycosidic linkages is higher than 12%, a method of preparing same, and an encapsulation agent comprising same as well as a method of encapsulating an active agent with said encapsulation agent.

14 Claims, 12 Drawing Sheets

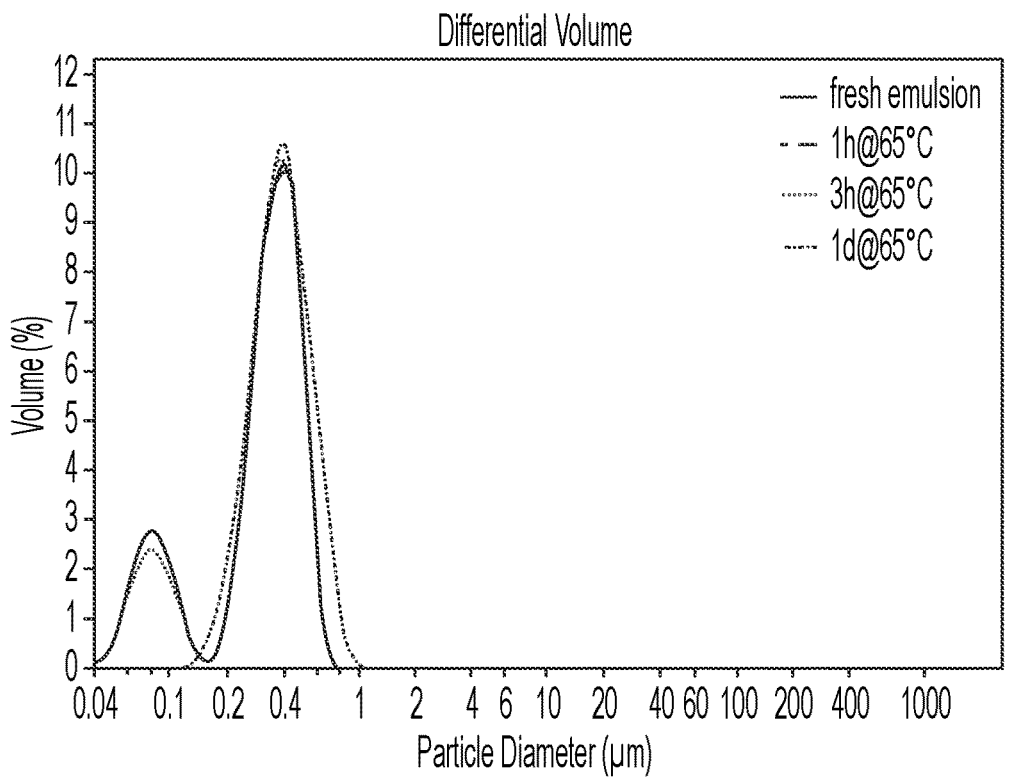
Fig. 1: OSA Starch 1 tempered 3h @150°C
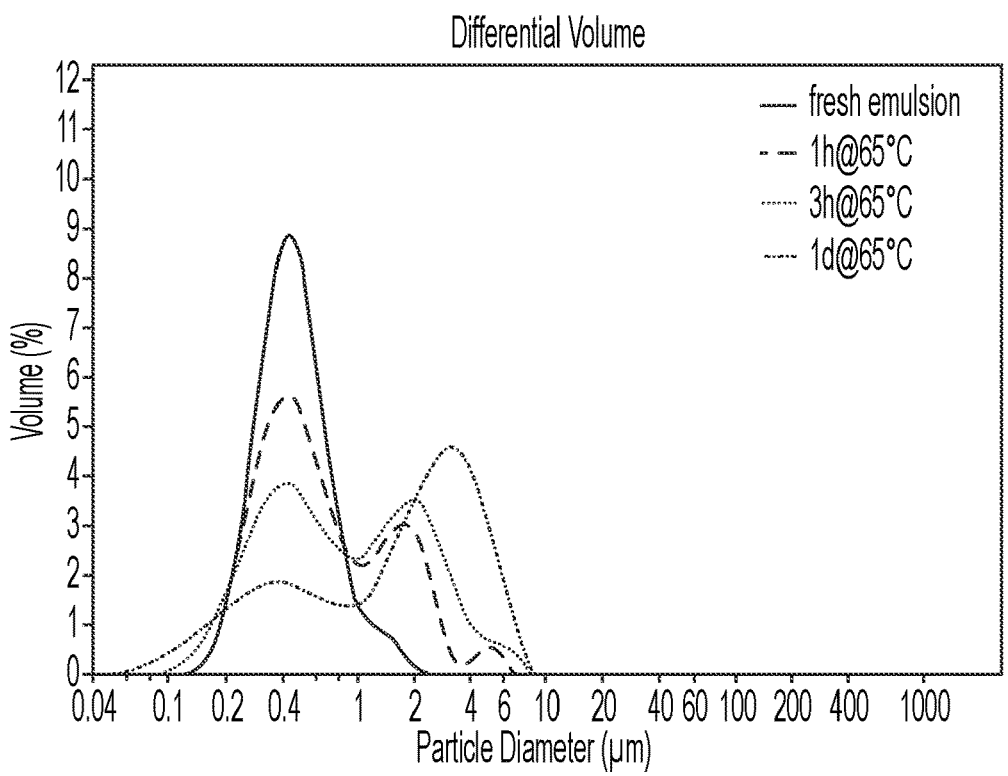
Fig. 2 OSA Starch 1 not tempered

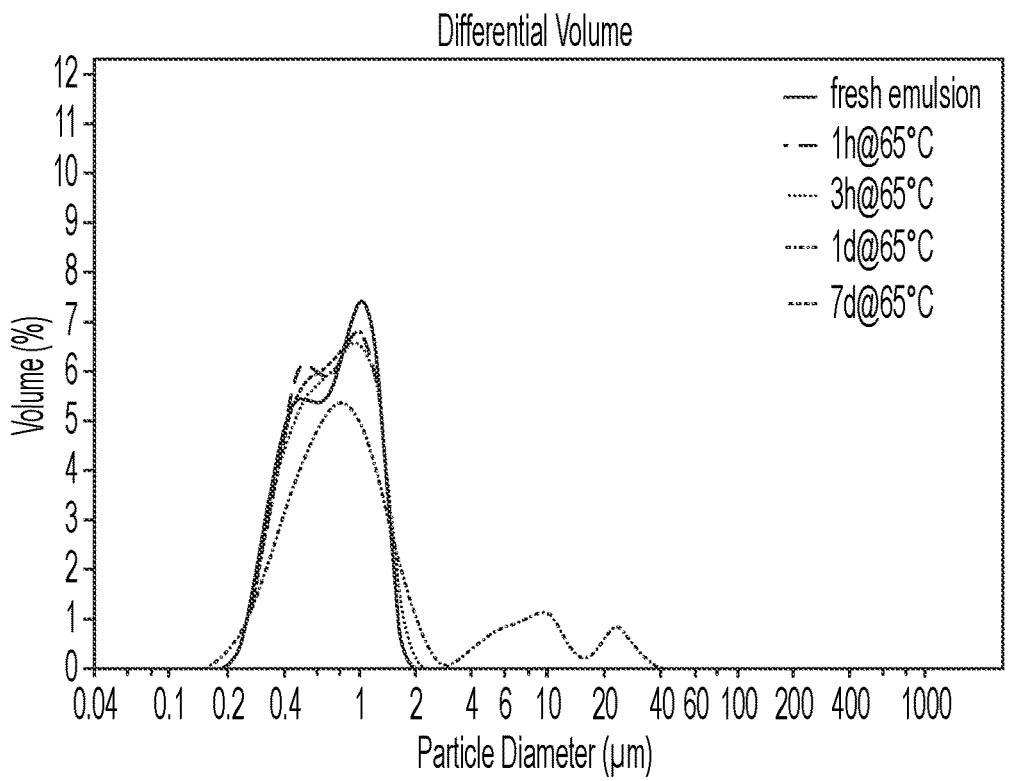
Fig. 3 OSA Starch 5 not tempered
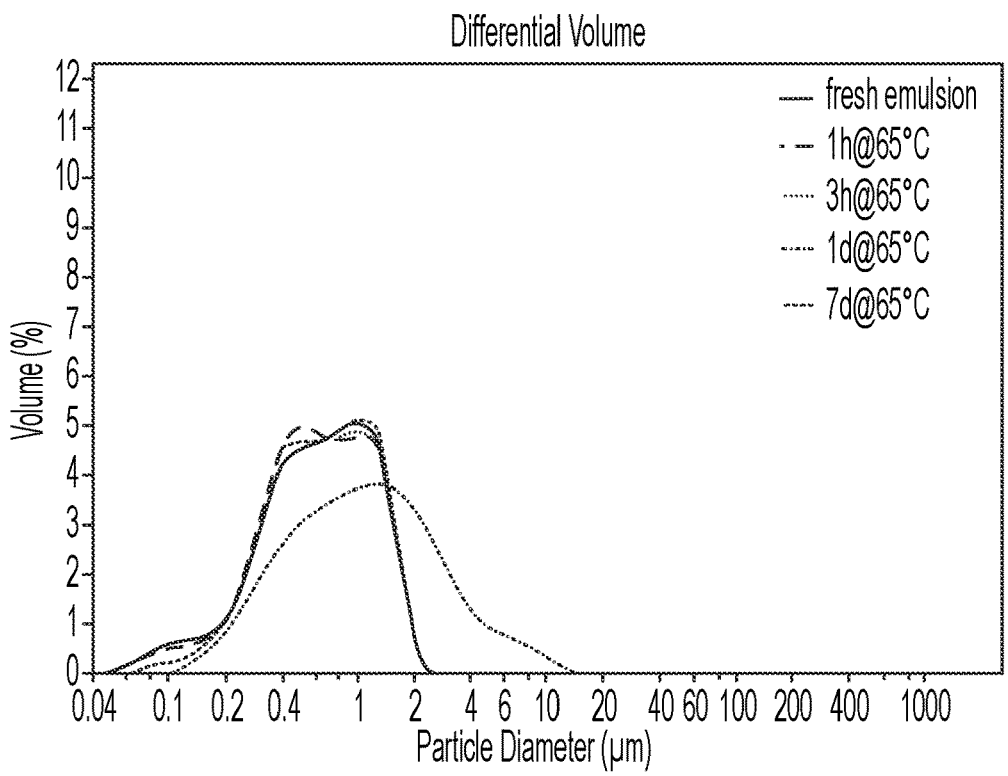
Fig. 4 OSA Starch 5 tempered 3h @150°C

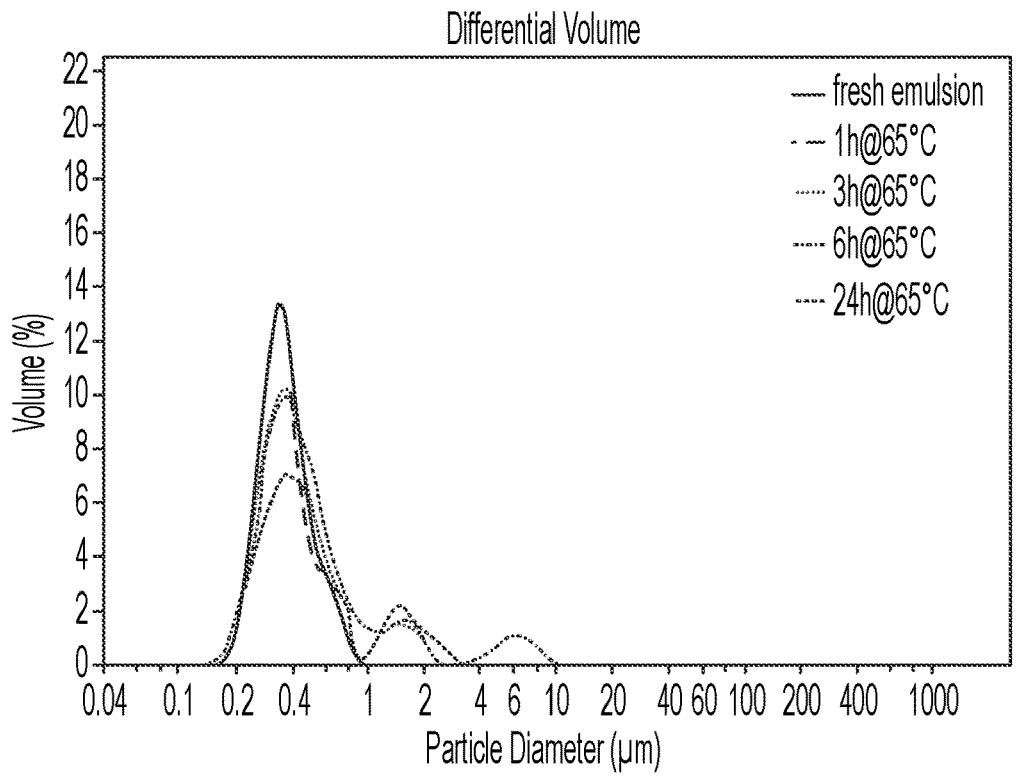
Fig. 5 OSA Starch 1 not tempered + β-carotene
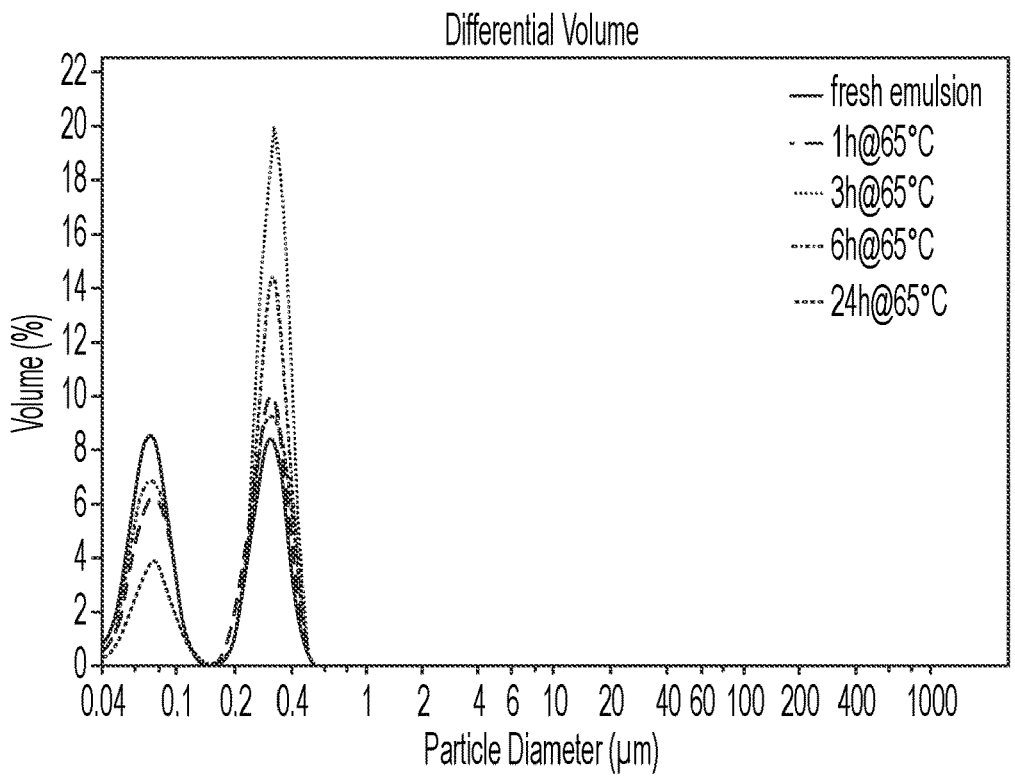
Fig. 6 OSA Starch 1 tempered + β-carotene

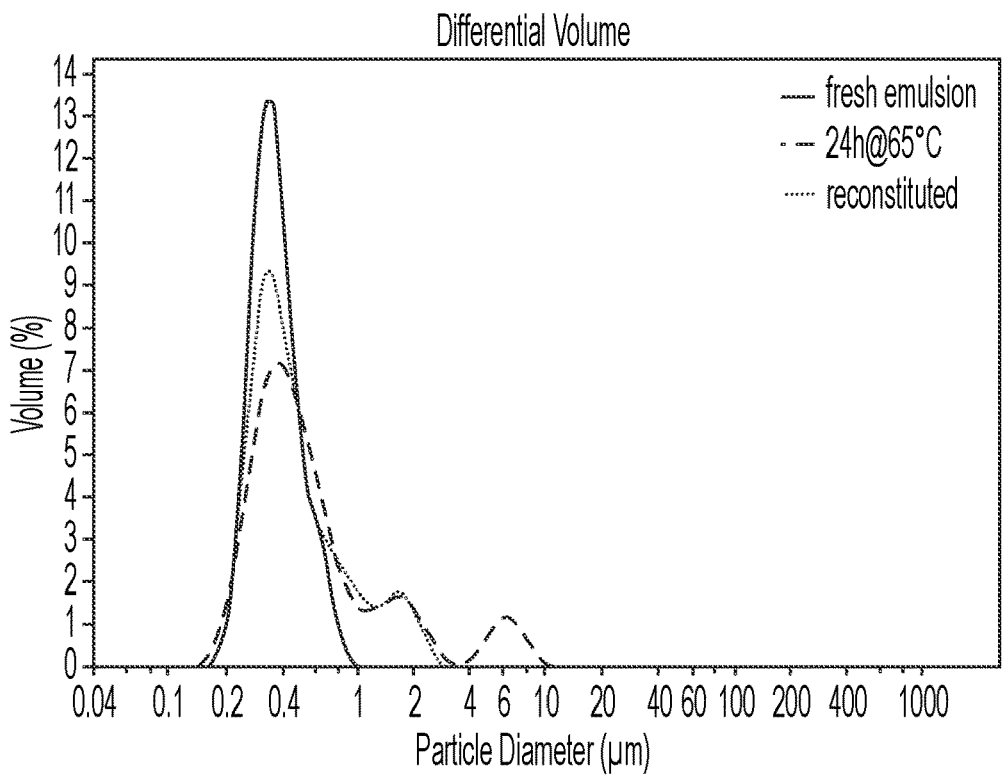
Fig. 7 OSA Starch 1 not tempered + β-carotene (spray-dried and reconstituted)
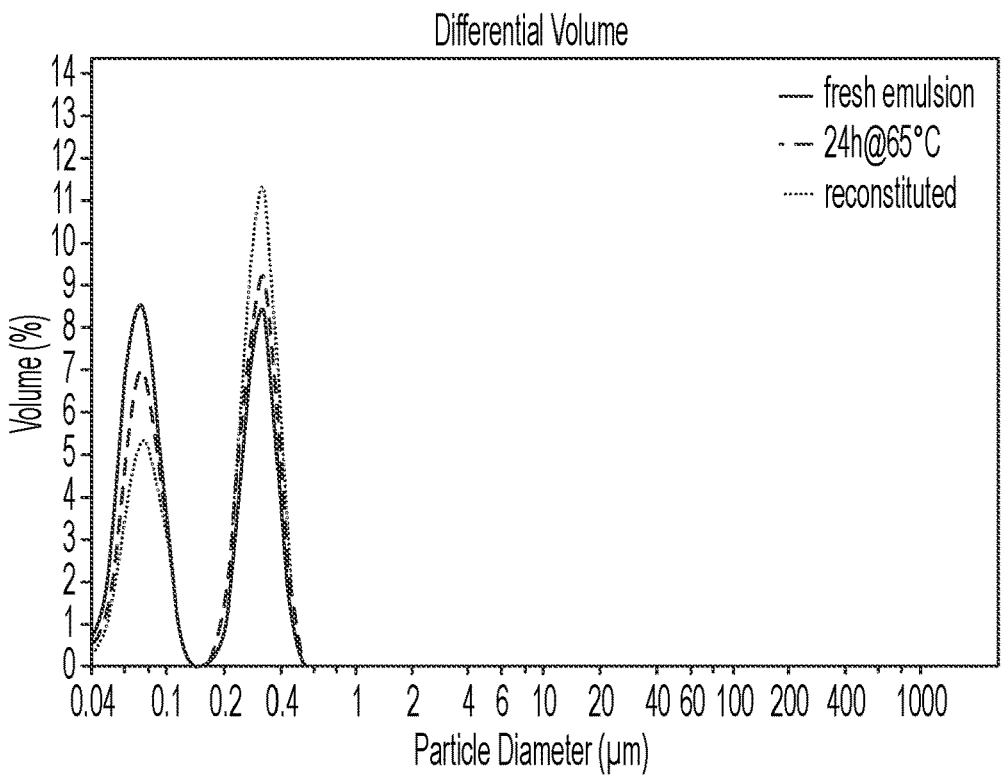
Fig. 8 OSA Starch 1 tempered + β-carotene (spray-dried and reconstituted)

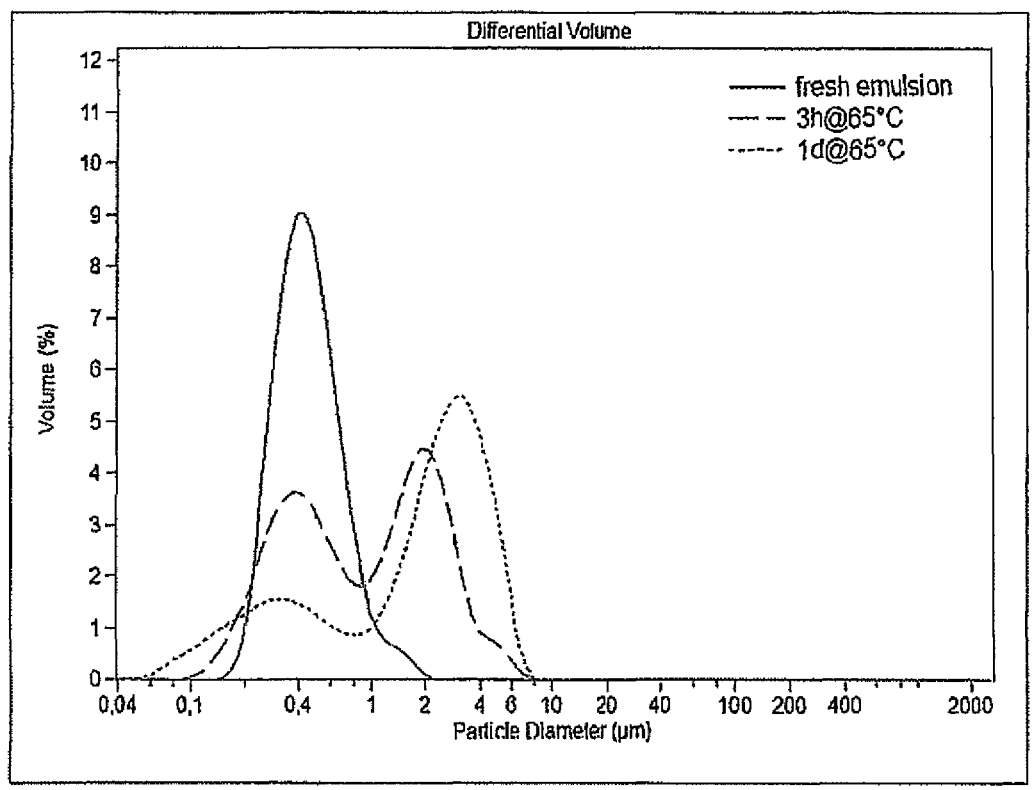
Fig. 9: 95% OSA Starch 1 not tempered + 5% OSA-maltose

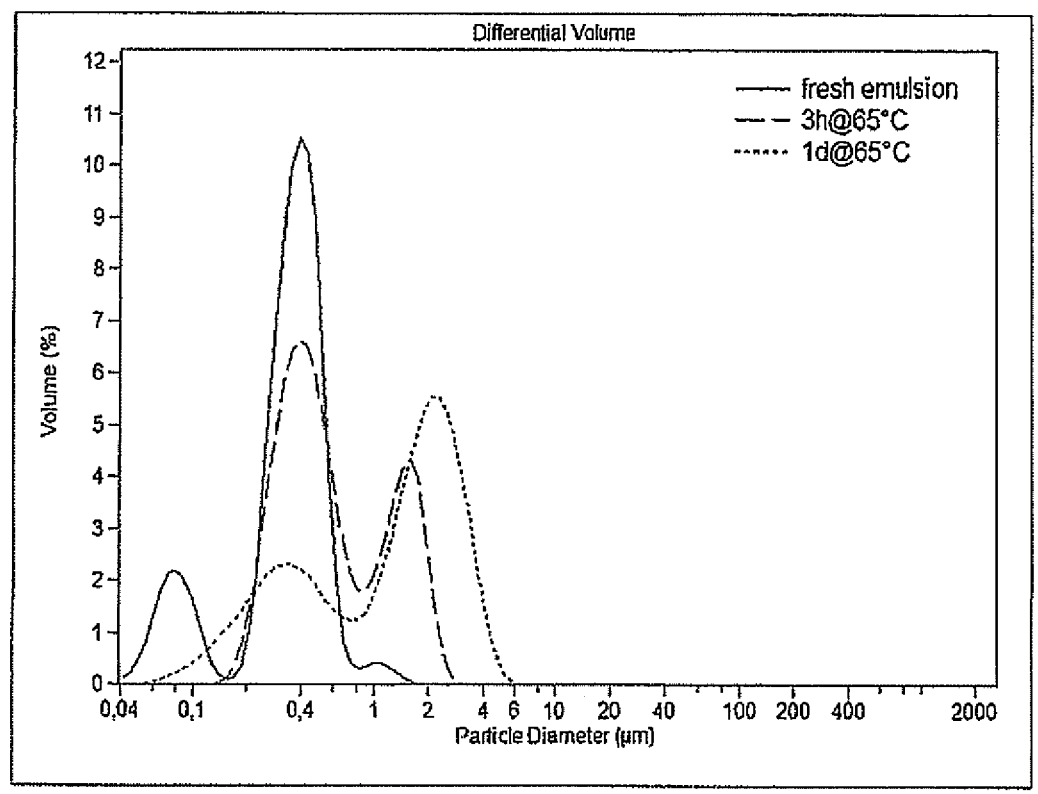
Fig. 10: 95% OSA Starch 2 not tempered + 5% OSA-maltose

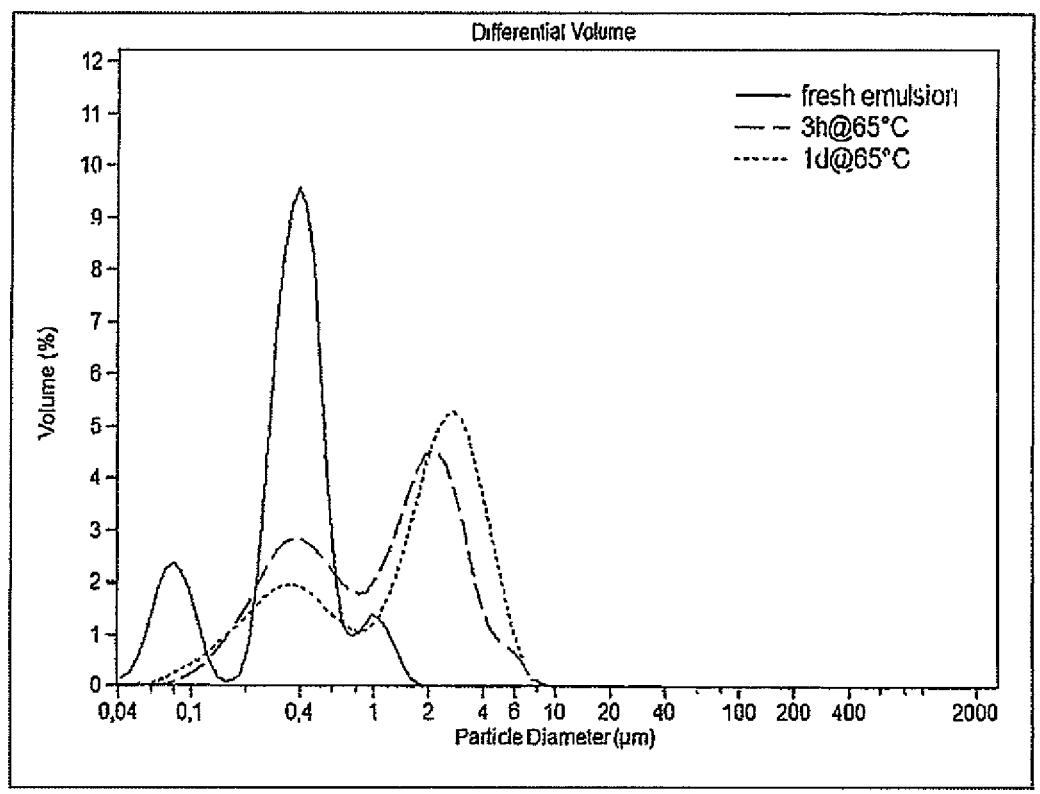
Fig. 11: 80% OSA Starch 1 not tempered + 20% OSA-maltose

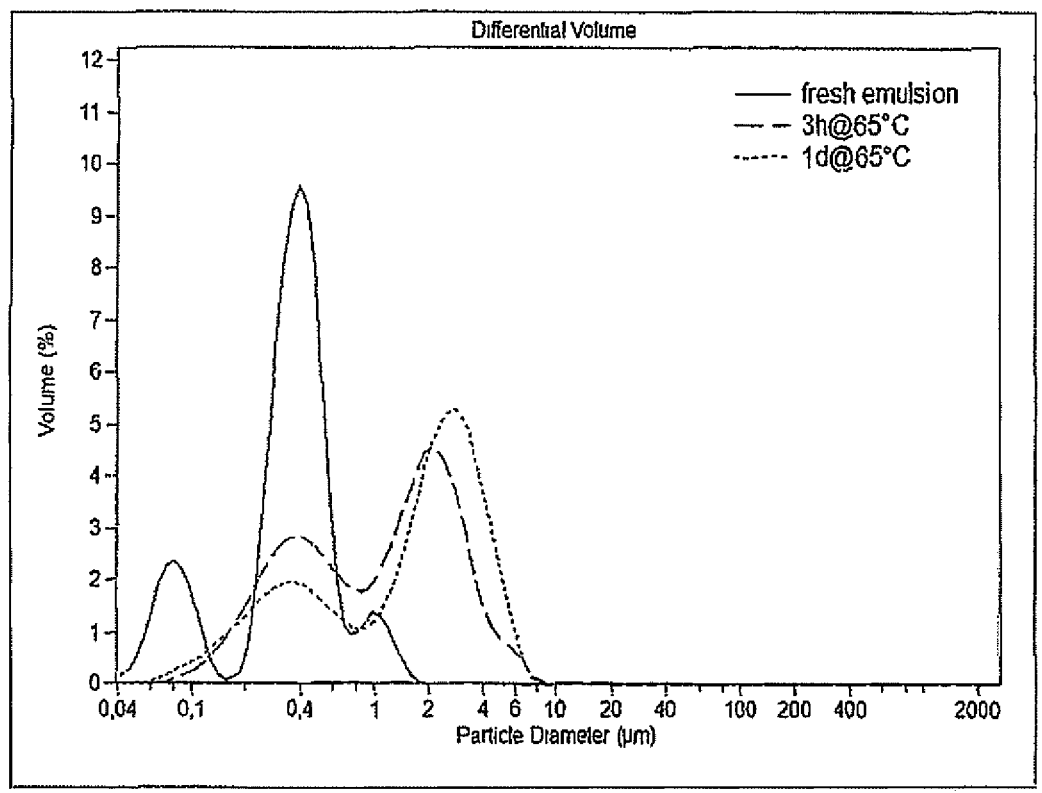
Fig. 12: 80% OSA Starch 2 not tempered + 20% OSA-maltose

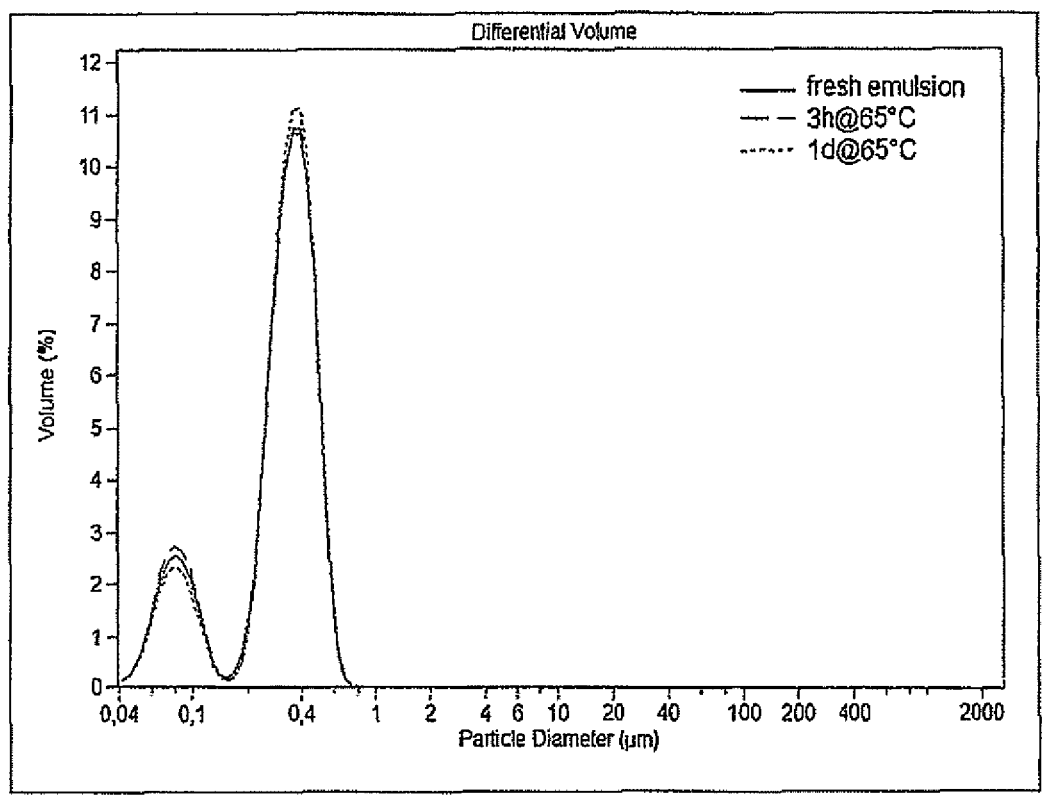
Fig. 13: 100% OSA Starch 2 tempered for 3 h@150°C

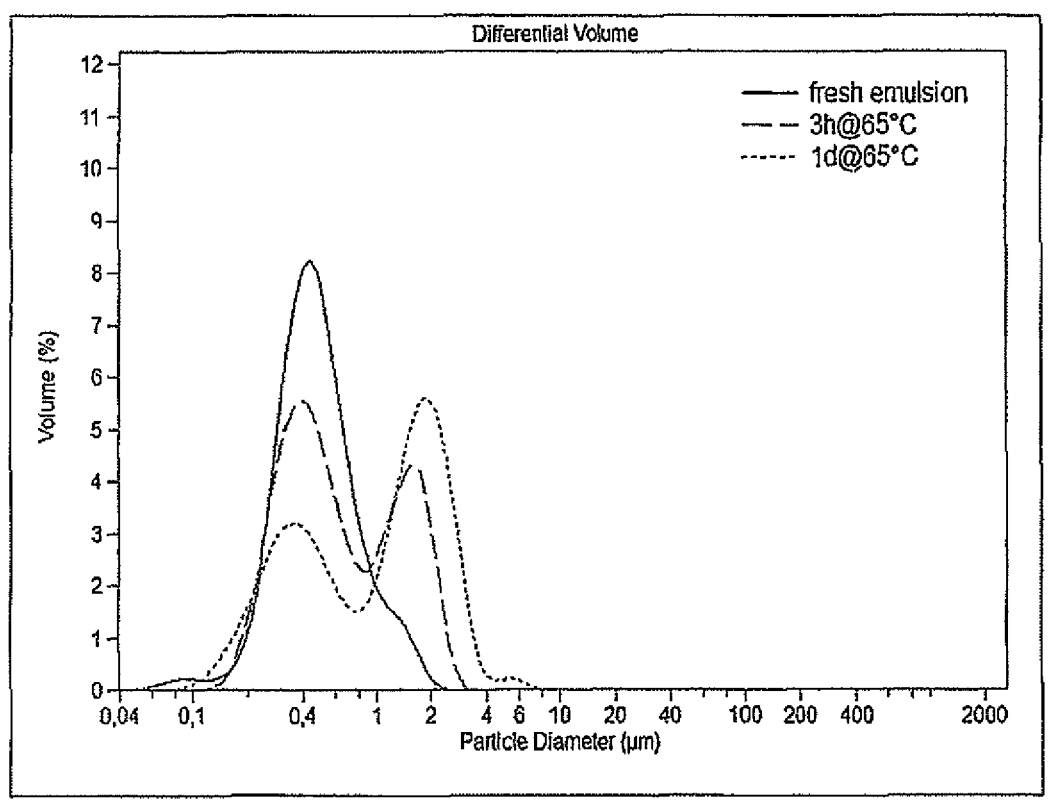
Fig. 14: 80% OSA Starch 2 tempered for 3 h@150°C + 20% OSA-maltose

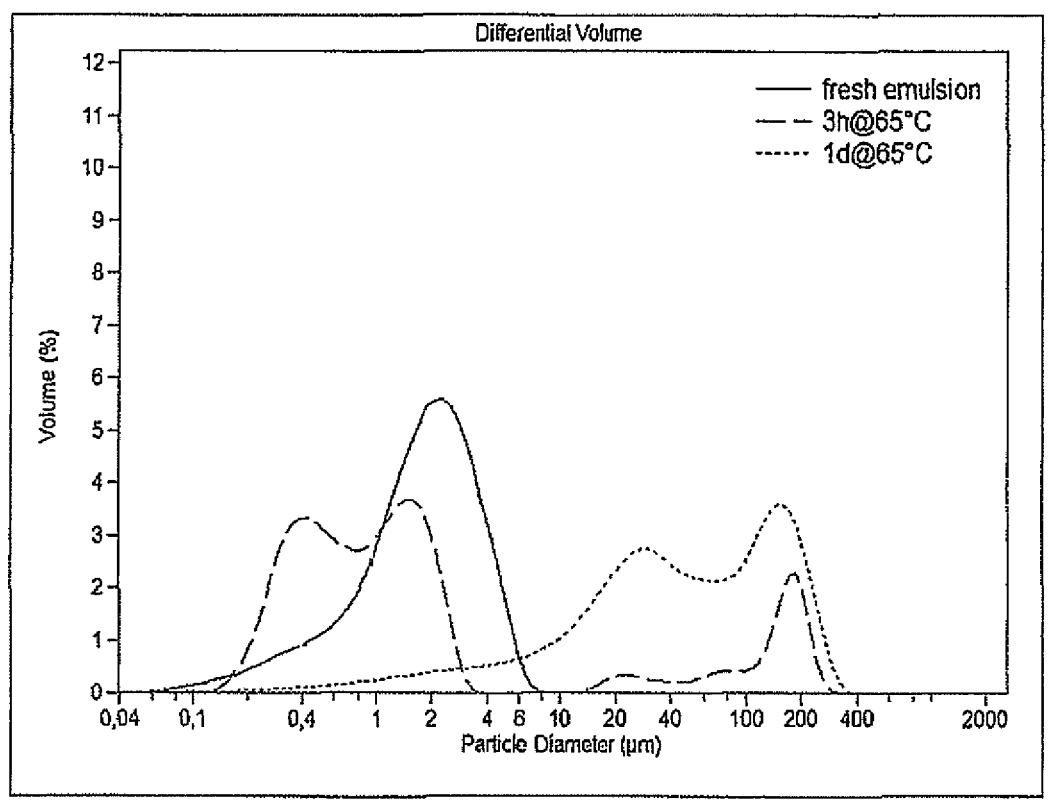
Fig. 15: 24% OSA-Maltose solids containing 0.72% OSA

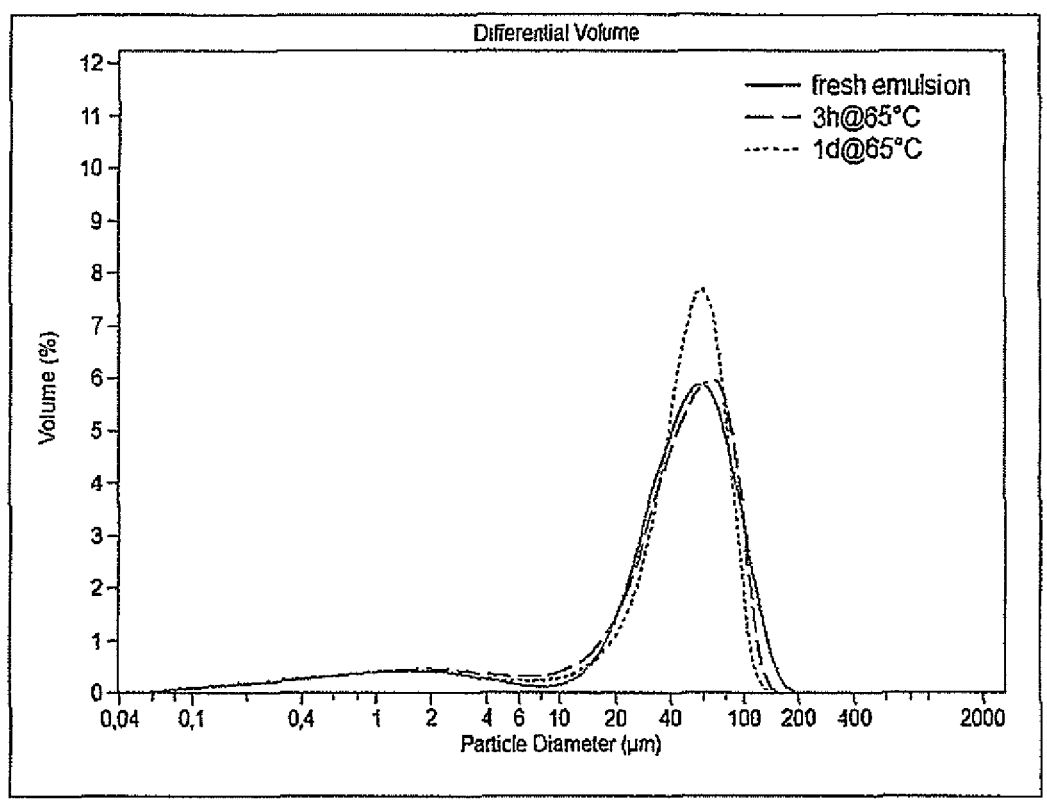
Fig. 16: 0.72% pure OSA

MODIFIED STARCH

CROSS-REFERENCE TO RELATED APPLICATIONS

This application is a U.S. National Stage under 35 U.S.C. § International Application No. PCT/US2018/041283 filed Jul. 9, 2018, which claims the benefit of priority from European patent application No. 17180478.4, filed Jul. 10, 2017, which is hereby incorporated herein by reference in its entirety.

The present invention relates to an octenyl succinic acid modified starch (OSA modified starch), a method for its preparation and an encapsulating agent comprising the modified starch.

A variety of chemical compositions are conventionally used as encapsulating and emulsifying agents, respectively, in inter alia, the food, cosmetic, paint, pharmaceutical, personal care, household and polymer industry. Typical compositions which conventionally function as an encapsulating agent include gum arabic, dextrins, modified starches, arabinogalactan, gum acacia, animal or plant proteins such as casein, gelatin, carboxymethyl cellulose, tragacanth, karaya, alginates such as sodium alginate, tannin and celluloses. Starches are of particular interest due to their easy availability. They have however the disadvantage of a high variance with respect to their efficiency as encapsulating agent and emulsifying agent, respectively.

U.S. Pat. No. 4,977,252 discloses modified starches that were obtained by enzymatic degradation with subsequent derivatization with a hydrophobic unit or a unit with hydrophobic and hydrophilic moieties. These starch derivatives are used as emulsifiers in industrial products, in particular in food and beverages.

EP 0 992 449 B1 describes a modified starch obtained after enzymatic hydrolysis of a starch molecule containing a hydrophobic or a hydrophobic and a hydrophilic group. This modified starch is used inter alia as an encapsulating agent in a variety of applications, including tablets.

U.S. Pat. No. 5,087,461 A discloses a spray dried composition encapsulated in an extruded glassy matrix, which comprises a chemically modified starch, a maltodextrine, a corn-syrup solid or polydextrose, and a mono- or di-saccharide.

US 2001/0287165 A discloses OSA modified starches and their use as encapsulating and emulsifying agents, respectively.

The drawback of these known modified starches is that they have a strong variability in their emulsifying ability. Further, the colloidal stabilization and/or protection of emulsified, dispersed and/or precipitated particles is not very strongly pronounced. Moreover, emulsions, dispersions and/or precipitates containing these starches have a limited thermal stability, especially over longer storage periods. Especially the ability to disperse and emulsify, respectively strongly decreases over longer periods of time. Additionally, it is not possible with the conventional modified starches to provide an emulsion, dispersion and/or precipitate having a relatively small particle size that is stable and also remains stable over a longer period of time.

It was the task of the present invention to overcome these disadvantages of the prior art. Especially it was the task of the present invention to provide a modified starch that has a high encapsulating and emulsifying ability, respectively, as well as a high ability of colloidal stabilization and/or protection of emulsified, dispersed and/or precipitated particles and that enables the preparation of emulsions, dispersions and/or precipitates having a relatively small particle size which are, and remain, stable. Further, these emulsions shall be storage stable over a longer period of time and in particular thermally stable over a longer period of time, i.e. no substantial changes in particle size shall occur, even when the emulsion, dispersion and/or precipitate is dried and reconstituted.

Surprisingly it was found that an OSA modified starch according to claim 1, wherein the OSA modified starch has been degraded by at least one enzyme capable of cleaving the 1,4-linkages of the starch molecule from the non-reducing ends to produce short chain saccharides, wherein the content of non-covalently bound, free octenyl succinic acid (also called residual octenyl succinic acid) in the OSA modified starch is less than about 0.50% by weight (determined by HPLC as set forth hereinafter), based on the total weight of the OSA modified starch, and wherein the content of the alpha-1,6-glycosidic linkages is higher than 12% is able to solve the above mentioned problems.

BRIEF DESCRIPTION OF THE DRAWINGS

FIG. 1 shows the particle diameter distribution for the tempered OSA Starch 1.

FIG. 2 for the not tempered OSA Starch 1.

FIG. 3 shows the particle diameter distribution for the tempered OSA Starch 5.

FIG. 4 for the not tempered OSA Starch 5.

FIG. 5 shows the particle size distribution for the not tempered OSA Starch 1.

FIG. 6 shows the particle size distribution for the tempered OSA Starch 1.

FIG. 7 shows the particle size distribution of the not tempered OSA Starch 1+β—carotene after reconstitution.

FIG. 8 shows the particle size distribution of the tempered OSA Starch 1+β—carotene after reconstitution.

FIG. 9 shows the particle size distribution for the mixture of 95% not tempered OSA Starch 1 plus 5% OSA-maltose.

FIG. 10 shows the particle size distribution for the mixture of 95% not tempered OSA Starch 2 plus 5% OSA-maltose.

FIG. 11 shows the particle size distribution for the mixture of 80% not tempered OSA Starch 1 plus 20% OSA-maltose.

FIG. 12 shows the particle size distribution for the mixture of 80% not tempered OSA Starch 2 plus 20% OSA-maltose.

FIG. 13 shows the particle size distribution of 100% OSA Starch 1 which was tempered for 3 h @150° C.

FIG. 14 shows the particle size distribution for the mixture of 80% OSA Starch 1 which was tempered for 3 h at150° C. plus 20% OSA-maltose.

FIG. 15 shows the particle size distribution of 24% OSA-maltose solids containing 0,72% OSA.

FIG. 16 shows the particle size distribution of 0.72% pure OSA.

The term "OSA modified starch" comprises all starches of a natural or a synthetic source that have been derivatized with octenyl succinic acid or an octenyl succinic acid derivative. "OSA-starch" is sometimes also referred to as "OSSA-starch".

Octenyl succinic acid (OSA) means oct-1-en-1-yl-succinic acid.

Octenyl succinic acid derivatives suitable for the derivatization of the starch comprise all octenyl succinic acid derivatives, which are reactive against the functional groups of the starch and which are able to react with said functional groups by forming an ester bond. Such octenyl succinic acid derivatives include but are not limited to octenyl succinic acid anhydride and octenyl succinic acid chloride, wherein octenyl succinic acid anhydride is preferred.

OSA modified starch is commonly known in Europe as additive having the numbers E1450 (starch sodium octenyl succinate) and E1452 (starch aluminum octenyl succinate).

All starches and flours are suitable for use herein and may be derived from any native source. A native starch or flour, as used herein, is one as it is found in nature, including those developed by plant breeding, and bioengineered starches. Typical sources for the starches and flours are cereals, tubers, roots, legumes and fruits. The native source can be corn or maize, respectively, pea, potato, sweet potato, banana, barley, wheat, rice, sago, amaranth, tapioca, arrowroot, canna, sorghum, and waxy or high amylose varieties thereof.

As used herein, the term "waxy" is intended to include a starch or flour containing at least about 90% by weight amylopectin, preferably about 95% by weight amylopectin, and most preferably about 98% by weight amylopectin. As used herein a high amylose content is defined as an amylose content of more than 45% by weight.

Also included as useful base materials are the conversion products derived from any of the above starches including fluidity or thin-boiling starches prepared by oxidation, enzymatic degradation or heat dextrinization.

Preferably the OSA modified starch is a modified starch on the basis of a waxy starch, more preferably on the basis of a waxy corn starch.

Methods for derivatization of the starch are well known in the art.

In order to obtain the OSA modified starch according to the present invention it is preferred to use octenyl succinic acid anhydride for the derivatization. As mentioned above, it is also possible to use other octenyl succinic acid derivatives suitable for the derivatization of the starch, i.e. all octenyl succinic acid derivatives that are reactive against the functional groups of the starch and that react with said groups by forming an ester bond.

The derivatization of the starch can be performed on the granule or in a dispersed and/or solubilized, pregelatinized or dissolved state.

Preferably, in order to derivatize the starch, the starch slurry can be adjusted to a pH of about 5 to about 11, more preferably of about 7 to about 8. Subsequently about 0.1 to about 100% by weight, preferably about 2 to about 5% by weight, based on the dry weight of the starch, of octenyl succinic acid anhydride can be added to the starch slurry. The mixture can then be heated at a temperature of about 20 to about 95° C. for about 0.1 to about 10 hours until the reaction is complete. The obtained OSA modified starch can subsequently be washed and dried.

After OSA derivatization of the starch, the starch is enzymatically degraded by an enzyme capable of cleaving the 1,4-linkages of the starch molecule from the non-reducing ends to produce short chain saccharides, with said saccharides being preferably mono- and/or di-saccharides resulting in a high oxidation resistance, when transferred to the intended use. At the same time the high molecular portions of the starch substantially remain, favoring the encapsulating properties.

Preferred enzymes useful in the present invention include but are not limited to β-amylase, glucoamylase, maltogenese, pullulanase, exo-alpha-1,4-glucosidase, exo-1,4-alpha-D-glucan maltotetrahydrolase, and/or exo-1,4-alpha-D-glucan-maltohexahydrolase, particularly β-amylase and/or glucoamylase. The enzymes used can contain up to 5% by weight impurities of other starch degrading enzymes, such as α-amylase.

The enzymatic degradation of the starch is carried out using techniques known in the art. The amount of enzyme used is dependent upon the enzyme, i.e., type, source and activity, and base material used, as well as the amount of degradation desired. Typically, the enzyme is used in an amount of from about 0.01 to about 1.0% by weight, particularly from about 0.001 to about 0.3% by weight, based on the weight of the starch.

The optimum parameters for enzyme activity will vary depending upon the enzyme used. The rate of enzyme degradation depends upon factors known in the art, including the type of enzyme used, enzyme concentration, substrate concentration, pH, temperature, the presence or absence of inhibitors, and the degree and type of modification. These parameters may be adjusted to optimize the degradation rate of the starch base.

The starch may be gelatinized before and/or after the enzyme degradation. The gelatinization process unfolds the starch molecules from the granular structure, thereby permitting the enzyme to more easily and uniformly degrade the starch molecules.

Generally the enzyme treatment is carried out in aqueous or buffered slurry at a starch solids level of about 10 to about 40% by weight, depending upon the base starch being treated. A solids level of from about 15 to about 35% by weight is particularly useful, a solids level from about 18 to about 25% by weight more particularly useful. In the alternative, the process may utilize an enzyme immobilized on a solid support.

Typically, enzyme degradation is carried out at the highest solids content feasible without reducing reaction rates in order to facilitate any desired subsequent drying of the starch composition. Reaction rates may be reduced by high solid contents as agitation becomes difficult or ineffective and the starch dispersion becomes more difficult to handle.

The pH and temperature of the slurry should be adjusted to provide effective enzyme degradation. These parameters are dependent on the enzyme used and are known in the art. In general, a temperature of about 22 to about 65° C., preferably of about 50 to about 62° C., is used. In general, the pH is adjusted to a The enzyme reaction is preferably continued until a dextrose equivalent of more than 30, preferably of about 30 to about 40, has been achieved, or until the desired end point (i.e., sufficient degradation to provide the desired functionality bout 3.5 to about 7.5, using techniques known in the art.

The enzyme reaction is preferably continued until a dextrose equivalent of more than 30, preferably of about 30 to about 40, has been achieved, or until the desired end point (i.e., sufficient degradation to provide the desired functionality The enzyme reaction is preferably continued until a dextrose equivalent of more than 30, preferably of about 30 to about 40, has been achieved, or until the desired end point (i.e., sufficient degradation to provide the desired functionality The enzyme reaction is preferably continued until a dextrose equivalent of more than 30, preferably of about 30 to about 40, has been achieved, or until the desired end point (i.e., sufficient degradation to provide the desired functionality for the particular application) has been reached. The end point may be determined by a change in viscosity, by the reducing sugar content (as measured for example by dextrose equivalents) or by any other method known in the art for measuring the level of enzyme degradation of the starch molecule. In general, the enzyme reaction will take from about 0.1 to about 24 hours, particularly from about 0.5 to about 4 hours. The time of the reaction is dependent on the type of starch and the enzyme used, the amount of the enzyme used, and the reaction parameters like solids content, pH, and temperature.

The enzyme degradation of the starch is then terminated by any technique known in the art such as acid or base deactivation, heat deactivation, ion exchange, and/or solvent extraction. For example, acid deactivation may be accomplished by adjusting the pH to lower than 2.0 for at least 30 minutes, or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The resultant solution is typically adjusted to the desired pH according to its intended end use, preferably by using HCl. The pH of a 5% by weight solution is preferably about 2 to about 4.7.

The OSA modified starch is typically dried using known methods, such as spray drying, microwave drying, fluidized bed drying, continuous fluidized bed drying, spray dripping, spray congealing, spray chilling, tray drying, drum drying, belt drying and/or freeze drying.

The content of non-covalently bound, free octenyl succinic add is particularly critical in the OSA modified starch of the present invention. The OSA modified starch according to the invention contains less than about 0.50% by weight, preferably less than about 0.45% by weight, more preferably less than about 0.40% by weight, most preferably less than about 0.30% by weight of non-covalently bound, free octenyl succinic acid, based on the total weight of the OSA modified starch, determined by the method described hereinafter.

As used herein, non-covalently bound, free octenyl succinic acid refers to the sum of the octenyl succinic acid and the respective octenyl succinic acid derivative that was used to derivatize the starch, which is not covalently or adsorptively bound to the carbohydrate chain, but is freely present in the modified starch.

The content of non-covalently bound, free octenyl succinic acid is determined as follows by HPLC.

Sample Preparation for Determining Non-Covalently Bound, Free Octenyl Succinic Acid:

In each case 125 mg of the OSA modified starch is weighed into a 20 mL vial, to which is added 15.0 mL of methanol. The vial is sealed and mixed for 18 h. The sample is diluted with water to yield a 2:1 water:methanol solution. The solution is filtered through a PVDF 0.45 μm filter and analyzed.

Sample Preparation for Determining the Total Content of Octenyl Succinic Acid:

In each case 20 mg starch is weighed into a 20 mL vial, to which is added 15.0 mL 0.05N KOH solution. The vial is crimp capped and heated at 75° C. for 3 h or until the starch is completely dissolved. The sample is allowed to cool, filtered through a filter, and collected for analysis.

Preparation of a Standard/Reference Material for the Analysis of the OSA Modified Starches:

20 mg of reference material, octenyl succinic acid anhydride (CAS No.: 42482-06-4), is weighed into a 20 mL vial to which is added 20 mL 0.1N KOH solution. The reference material is heated in the sealed vial at 75° C. for 3 h until the octenyl succinic acid anhydride is completely dissolved. Secondary standards are prepared by diluting stock solution using 33/67 methanol/water mixture producing standards in the range of 0.2 to 20 μm/mL OSA.

Analysis was carried out using Empower-HPLC

Mobile phase: Channel A, 1.0% phosphoric acid aqueous solution

Channel B, acetonitrile

Flow Rate: 0.3 mL/min

Column: Cortecs C18 2.7 μm, 2.1×100 mm

Column Temperature: 40° C.

UV Detection Wavelength: 205 nm

Analysis Time: 20 min

Injection Volume: 5.0 μL

Retention time: 5.5 min and 6.0 min

The content of covalently bound octenyl succinic acid is calculated as the difference between the total content of octenyl succinic acid, and the content of non-covalently bound, free octenyl succinic acid and octenyl succinic acid derivative.

As used herein, covalently bound octenyl succinic acid is understood as octenyl succinic acid that is bound to the carbohydrate chain via an ester bond.

As used herein, the total content of octenyl succinic acid is understood as the sum of the octenyl succinic acid bound covalently to the starch and the non-covalently bound, free octenyl succinic acid.

In a case where a content of about 0.50% by weight of non-covalently bound, free octenyl succinic acid is exceeded, this is disadvantageous because the non-covalently bound, free octenyl succinic acid is able to further react with itself or other carbohydrate parts of the starch, which negatively influences the molecular three-dimensional geometry of the modified starch. Further, an excess of non-covalently bound, free octenyl succinic acid in the modified starch negatively affects the surface activity of the OSA modified starch resulting in a worse emulsion and dispersion activity, respectively, of the OSA modified starch, when transferred to the intended use.

It is further commonly known to determine the content of non-covalently bound, free octenyl succinic acid according to the method described in "JECFA INS No. 1450". The values determined by this method are usually lower compared to the values obtained by the above described HPLC method. All values presented in the present invention have been determined using the above described HPLC method.

The OSA modified starch according to the present invention has preferably a dextrose equivalent (DE) of more than about 20. Preferred is a dextrose equivalent of about 24 to about 40, more preferred of about 26 to about 40, even more preferred of about 28 to about 40 and most preferred of about 30 to about 40.

The dextrose equivalent (DE) is defined as the reduction capacity of the starch hydrolysate. Each starch molecule has one reducing end. Therefore, DE is inversely related to the molecular weight. The DE value of anhydrous D-glucose is defined as 100 and the DE value of non-hydrolyzed starch is close to zero. The dextrose equivalent was determined as follows.

The dextrose equivalent was determined by the titration method for total sugars #-10-9070 under the NF 22 monograph for noncrystallizing sorbitol solution. In duplicate 0.05 or 0.10 g starch was accurately weighed into an Erlenmeyer flask and brought to weight of 50 g with deionized water, to which was added 50 mL cupric sulfate iodide. The solution was gently refluxed on a hot plate for 5 min and then cooled to room temperature. Thereafter 25 mL 5N sulfuric acid was added slowly with constant stirring. The solution was then titrated with 0.1N sodium thiosulfate and starch indicator to reach a sky blue equivalent point. Reducing sugar (%) was calculated by subtracting the volume of titrant in the blank form from the volume of titrant in the sample, converting the mL titrant into mg of sugar from the #J-10-9070 reference table, and dividing the mg sugar by 10 times the grams of sample used.

OSA modified starches having higher DE values have the disadvantage that they exhibit a high hygroscopicity as well as a disadvantageous powder flowability, a low Tg-value, a disadvantageous drying behavior, a lower viscosity of the resulting solution, emulsion and/or dispersion, and a potentially low storage stability.

OSA modified starches having lower DE values have the disadvantage to provide merely inferior oxidation stability, a higher viscosity of the resulting solution, emulsion and/or dispersion, a lower dry solids content in drying processes, and a lower solubility.

Preferably, the content of covalently bound octenyl succinic acid in the OSA modified starch is from about 0.1% to about 10% by weight, more preferably from about 0.5 to about 5% by weight and most preferably from about 2 to about 3% by weight, based upon the total weight of the OSA modified starch.

A higher degree of substitution is relatively costly, thus the cost benefit value is relatively unfavorable.

The OSA modified starch according to the present invention is preferably a waxy starch, more preferably a waxy corn starch.

The content of amylopectin in the waxy corn starch is preferably more than about 90% by weight, more preferably more than about 95% by weight, and even more preferably more than about 98% by weight, based on the total weight of the base starch.

Besides a waxy corn starch, other starches with a content of amylopectin of more than about 90% by weight, preferably more than about 95% by weight, and even more preferably more than about 98% by weight, based on the total weight of the base starch, are suitable herein.

Starches with a content of amylopectin of less than 90% by weight tend to gel and have a worse emulsifying activity and are thus disadvantageous.

The content of amylose in the waxy corn starch is preferably less than about 10% by weight, more preferably less than about 5% by weight and even more preferably less than about 2% by weight, based on the total weight of the OSA modified starch.

Besides a waxy corn starch other starches with a content of amylose of less than about 10% by weight, more preferably less than about 5% by weight and even more preferably less than about 2% by weight, based on the total weight of the OSA modified starch, are suitable herein.

Waxy corn starches with a content of amylose higher than about 10% by weight tend to gel and have a worse emulsifying activity and are thus disadvantageous.

The OSA modified starch according to the present invention has a content of alpha-1,6-glycosidic linkages of more than about 12%, preferably of more than about 12.5%. Even more preferably are contents of more than about 13%. The content of alpha-1,6-glycosidic linkages is determined using high-temperature $^1$H-NMR.

The solid samples were dissolved in $D_2O$/TSP-$d_4$ on a steam bath and $^1$H-NMR spectra were measured at 90° C. using a Bruker Avance III HD 400 MHz NMR instrument at 400 MHz. TSP-$d_4$ was added as internal standard.

OSA modified starch having a content of alpha-1,6-glycosidic linkages of more than about 12%, more preferably of more than about 12.5%, even more preferably of more than about 13% have the advantage that the emulsifying activity is increased.

The OSA modified starch according to the present invention preferably has a viscosity of about 40 to 150 mPas, more preferably of about 50 to 100 mPas in a 28.57% by weight aqueous solution of the OSA modified starch. The viscosity was determined on a Brookfield viscometer, using spindle 3 at 100 rpm at 20° C., if not specified differently.

Further, the OSA modified starch according to the present invention has a weight average molecular weight ($M_w$) of the starch portion from about 70,000 to 250,000 Da, preferably from about 110,000 to 220,000 Da. The average molecular weight of the starch portion was determined as follows.

The OSA modified starch was dissolved in DMSO overnight and subsequently heated at about 95 to 100° C. for 1 h followed by cooling the solution.

The obtained solution was filtered through a 0.45 μm PP membrane and the molecular weight was determined by gel permeation chromatography using the following parameters.
Column set: Phenogel™ 10 μm 100 Å, $10^3$ Å, $10^5$ Å
Guard column: Phenogel™ 10 μm
Injection volume: 100 μL
Number of Injections: 2/sample
Standards: Pullulan (788 K-180 Da)
Sample concentration: 10.3-10.8 mg/4 mL
Detector: RID-10A from Shimadzu
Column Temperature: 60° C.
Mobile-phase: DMSO 4-0.03 M $NaNO_3$
Flow rate: 1 mL/min
Run time: 45 min It is preferred that the weight average molecular weight ($M_w$) of the starch portion increases more than about 10%, preferably more than about 20%, during tempering for 3 h at 150° C. Moreover, it is preferred that the weight average molecular weight ($M_w$) of the low molecular weight portion increases more than about 10%, preferably more than about 20%, during tempering for 3 h at 150° C.

As mentioned above, the OSA modified starch according to the present invention has been degraded by at least one enzyme capable of cleaving the 1,4-linkages of the starch molecule from the non-reducing ends to produce short chain saccharides. The selection of the enzymes does not require any special limitations. Preferred are enzymes selected from the group consisting of β-amylase, glucoamylase, pullulanase, maltogenase, exo-alpha-1,4-glucosidase, exo-1,4-alpha-D-glucan maltotetrahydrolase, and exo-1,4-alpha-D-glucan-maltohexahydrolase, with β-amylase and glucoamylase being preferred and β-amylase being most preferred. The enzymes used can contain impurities up to 5% by weight of other starch degrading enzymes, such as α-amylase.

OSA modified starch that was not enzymatically degraded, but e.g. acid hydrolyzed, is not suitable. OSA modified starches that have been hydrolyzed using an acid are forming emulsions having a significantly higher average particle diameter and are further not thermostable. Moreover, those starches exhibit a relatively low colloidal stabilization and/or protection and a low oxidative resistance to the encapsulated active ingredients.

An aqueous solution of the OSA modified starch according to the present invention has preferably a low surface tension. Preferably a 0.1% by weight aqueous solution of the OSA modified starch according to the present invention has a surface tension of less than about 50 mN/m, preferably of less than about 45 mN/m. A 0.5% by weight aqueous solution of the OSA modified starch according to the present invention preferably has a surface tension of less than about 40 mN/m, more preferably of less than about 36 mN/m.

The surface tension was thereby determined as follows:

Samples of the OSA modified starch were suspended in distilled water and stirred over-night with a magnetic stirrer. On the day of measurement, further dilutions of the stock solution were prepared and the surface tension was determined with a Kruess-tensiometer K11 MK3 using the plate method at 20° C. Values were recorded every 60 s for 10 min. Samples were measured up to four times. Differences between the samples were analyzed with a single factor variance with post-hoc test according to Fisher, Missing values were extrapolated for evaluation.

The low surface tension of an aqueous solution of the OSA modified starch according to the present invention results in an increased emulsifying activity as well as an increased wetting behavior and occupancy, respectively of the colloidal or fine-disperse surfaces. Further, solid/liquid-, liquid/liquid- or gaseous/liquid-interfaces are obtained that are beneficial for stabilizing micro- or nano-dispersions or-emulsions as well as foams.

The OSA modified starch according to the present invention is preferably further characterized by its color and the fact that the color does not substantially change during tempering.

The color values of the OSA modified starch were determined in the C:I:E:-LAB-Color-space. The L-axis defines the brightness of a color, the $\alpha$-axis the red-green-content and the b-axis the yellow-blue content. L-values are always positive and lie between 0 for ideal black colors and 100 for ideal white colors.

The color of the starch was determined using a Hunter ColorQUEST Spectrocolorimeter Sphere Model as follows.

The Hunter ColorQUEST Spectrocolorimeter Sphere Model was switched on two hours prior to use and was calibrated using the function "standardization". Subsequently, about 4 g of the OSA modified starch according to the present invention was deposited in the measuring cell and the L-, a- and b-values were determined.

The invention further relates to a method for preparing the OSA modified starch according to the present invention.

The method comprises the steps of:

a) providing an OSA modified starch, wherein the OSA modified starch has been degraded by at least one enzyme capable of cleaving the 1,4-linkages of the starch molecule from the non-reducing ends to produce short chain saccharides, and b) tempering the OSA modified starch at a temperature of about 50° C. to about 180° C. for about 0.1 h to about 8 h.

Preferably, the OSA modified starch is tempered in step b) at a temperature of about 80° C. to about 160° C. for about 0.2 to about 5 h, more preferably for about 0.5 to about 4 h and most preferably for about 2 to about 4 h.

Tempering at lower temperatures does not substantially reduce the content of non-covalently bound, free octenyl succinic acid in the OSA modified starch and is thus disadvantageous.

Tempering at higher temperatures and longer tempering has the disadvantage that, although the content of non-covalently bound, free octenyl succinic acid in the OSA modified starch is further reduced, other undesirable properties, like increase in viscosity and discoloration begin to superpose the beneficial properties of the OSA modified starch having a low content of non-covalently bound, free octenyl succinic acid in the OSA modified starch.

As used herein, tempering means heating of the OSA modified starch in a solid form. Preferably, the heating is carried out as a substantially dry heating. Preferably, the moisture content of the OSA modified starch is less than about 78-80%, even more preferably less than 40% by weight, more preferably less than about 25% by weight, even more preferably less than about 20% by weight, even more preferably less than about 10% by weight, and most preferably less than about 1-2% by weight, based on the total amount of the OSA modified starch as a dry solid.

It is further preferred that no further substances, like salts, acids, bases, further sugars or carbohydrates, are additionally added to the OSA modified starch before or during the tempering. It is especially preferred not to add bases, like $Na_2CO_3$, $NaHCO_3$, $NH_4HCO_3$, $(NH_4)_2CO_3$, or mixtures thereof, to the OSA modified starch before or during the tempering process. It is further especially preferred not to add short-chain saccharides or monosaccharides, especially glucose, maltose and/or sucrose to the OSA modified starch before or during the tempering process.

The tempering can be carried out in any suitable apparatus and is not limited to any special apparatus. Suitable apparatus are for example usual drying cabinets, fluid bed dryers, infrared dryers, microwave dryers and/or spray dryers.

Preferably, the OSA modified starch is stirred and/or mixed from time to time during the tempering in order to prevent the starch from baking together and from forming undesired clumps.

It is further preferred that the tempering is carried out under normal air-pressure (about 1 atm) or reduced pressure, whereby normal air-pressure is preferred.

It Is preferred that a 5% by weight aqueous solution of OSA modified starch according to the present invention has a pH prior to the tempering of less than about 7, preferably of less than about 6, and more preferably of less than about 4.7 measured at ambient temperature (15° C. to 25° C.).

After tempering, the OSA modified starch according to the present invention is cooled down to a temperature of about −20° C. to 50° C., preferably to a temperature of about 15 to 25° C. This cooling down can be carried out by any suitable method known in the art, like simple cooling down while standing at ambient temperature.

The powder properties of the OSA modified starch according to the present invention, i.e. powder flowability, bulk density, tamped density, Haussner-factor, angle of repose, granulometry and compaction ability, are not substantially affected by the tempering.

OSA modified starches with higher DE values have the disadvantage that they exhibit a high hygroscopicity, a disadvantageous powder flowability, a low Tg-value, a disadvantageous drying behavior, a low viscosity of the resulting solution, emulsion and/or dispersion, and a low storage stability of the emulsion dispersion and/or precipitate.

OSA modified starches with lower DE values have the disadvantage of inferior oxidation resistance of the emulsion or dispersion made thereof, a higher viscosity of the resulting solution, emulsion and/or dispersion, a lower dry solids content, and a lower solubility.

The invention further relates to an OSA modified starch obtainable by the method described above.

All properties described above for the OSA modified starch also concern the OSA modified starch obtainable by the method described.

The OSA modified starch obtained by the method according to the present invention has a content of alpha-1,6-glycosidic linkages of more than about 12%, more preferably of more than about 12.5%. Even more preferably are contents of more than about 13.

It is preferred that the OSA modified starch obtained by the method according to the present invention is characterized in that the content of the covalently bound octenyl succinic acid in the OSA modified starch is from about 0.1% to 10% by weight (determined by HPLC as set forth above), based on the total weight of the OSA modified starch.

It is furthermore preferred that the OSA modified starch obtained by the method according to the present invention is characterized in that the content of the covalently bound octenyl succinic acid in the OSA modified starch is from about 0.5% to about 5% by weight (determined by HPLC as set forth above), based on the total weight of the OSA modified starch.

It is preferred that the OSA modified starch obtained by the method according to the present invention is characterized in that the content of covalently bound octenyl succinic acid in the OSA modified starch is from about 0.5 to about 3% by weight, preferably 2% to about 3% by weight, (determined by HPLC as set forth above), based on the total weight of the OSA modified starch.

It is preferred that the OSA modified starch obtained by the method according to the present invention comprises an OSA modified waxy starch, preferably an OSA modified waxy corn starch.

It is preferred that the OSA modified starch obtained by the method according to the present invention is characterized in that the enzyme that is capable of cleaving the 1,4-linkages of the starch molecule from the non-reducing ends to produce short chained saccharides, is selected from the group consisting of β-amylase, glucoamylase, pullulanase, maltogenase, exo-alpha-1,4-glucosidase, exo-1,4-alpha-D-glucan maltotetrahydrolase and exo-1,4-alpha-D-glucan-maltohexahydrolase, preferably is β-amylase or glucoamylase, most preferably β-amylase.

It is further preferred that the OSA modified starch obtained by the method according to the present invention is characterized in that wherein a 0.5% by weight aqueous solution of the OSA modified starch has a surface tension of less than about 40 mN/m.

The invention further relates to an encapsulating agent comprising the OSA modified starch according to the present invention and/or the OSA modified starch obtained by the method described above.

The invention further relates to a method for emulsifying or encapsulating an active agent, comprising the above described as emulsifying or encapsulating agent.

The method comprises the steps of:
a) forming a solution or dispersion of the emulsifying or encapsulating agent; and
b) emulsifying, dispersing and/or precipitating the active agent in the solution formed in a).

The active agent may be any substance which will not react with the starch system, including but not limited to oils and fats, such as unsaturated fatty acids, flavors, colors, such as carotenoids, preferably β-carotene, fragrances such as terpenes, vitamins, and pharmaceuticals.

In particular, the OSA modified starch of the present invention is useful for encapsulating lipophilic, oil- or wax-based or oil-soluble active agents such as flavor oils and vitamins. These active agents may be volatile or nonvolatile and are generally characterized by being water immiscible but dispersible (emulsifiable) in water in the presence of an encapsulating agent.

In the case of oil as an active agent, the encapsulating agents according to the present invention also retain the oil so as to provide low surface oil. This is particularly true when glucoamylase and/or β-amylase are used to enzymatically hydrolyze the starch. The surface oil may be measured by methods known in the art such as by washing the encapsulated powder with a suitable solvent. Reduction of surface oil is important as increased surface oil indicates that the load of the active agent is not being maintained, and inefficiency of encapsulation. Thus, reduction of surface oil results in a longer shelf life. The encapsulating agent according to the present invention also provides a relatively high level of oxidation resistance, thereby prolonging storage stability of the encapsulated product and shelf life of the final product. Further, the active agent is protected against oxidation as well as against loss in case the agent is volatile. Also the invention enables an improved color intensity and stability of finely dispersed actives such as carotenoids in the encapsulates over a long time period also when re-dispersed in aqueous systems such as colored beverages.

The encapsulated product obtainable by using the encapsulating agents according to the present invention consistently achieves and maintains a relatively high load level of the active agent. The load level of the active agent realized may be greater than 150% by weight, preferably greater that 120% by weight, particularly greater than 100% by weight, more particularly greater than 80% by weight, based on the weight of the encapsulating agent. Moreover, the load level in the final encapsulated powder can be adapted to the intended use which depends on the active agent. The load level in the final encapsulated powder is preferably equal or higher than 1% by weight, more preferably higher than 5% by weight and most preferably higher than 55% by weight. The level of active agent retained may be determined by methods known in the art such as by hydro-distillation and solvent extraction in the case of flavor oils or by solvent extraction alone in the case of vitamins.

A high load level of active agent is desirable to reduce the cost of producing the final product as encapsulating agents are often expensive. Further, some encapsulating agents may contribute adverse or undesirable properties to the final system and it is thus desirable to reduce the amount of encapsulating agent used.

It is desirable not only to achieve a high load of active agent, but also to maintain it so as to enable a longer shelf life. Many active agents are volatile and/or labile, particularly flavors and fragrances. When the active agents are not encapsulated, they may be lost, producing undesirable variations in taste and aroma of the final products as perceived by the consumer. In addition, losses of such components increase the cost of the final products since it is necessary to increase the amount of the volatile/labile component to compensate for the losses which occur, and many are expensive. The encapsulating agents according to the present invention also provides a relatively high level of oxidation resistance, thereby prolonging storage stability of the encapsulated product and shelf life of the final product. Oxidation resistance may be measured by methods known in the art. For example, oxidation resistance of encapsulating agents containing citrus oil may be determined by using gas chromatography (GC) to measure the amount of oxidization products of limonene, such as carvone, carviol, or limonene oxide, present in the oil extracted from powders aged at 50° C. for two weeks. Less than about 0.8% carvone typically indicates acceptable levels of oxidation. Oxidation resistance is important not only for flavor considerations of the oil, but also to maintain the activity of various vitamins. To further increase oxidation resistance, at least one anti-oxidant may be added to the oil.

The resulting encapsulated product can be used in any desired amount in the final product, wherein this amount is dependent on the amount of the active agent encapsulated. Typically, the encapsulating agent and/or the final encapsulated material comprising the OSA modified starch according to the present invention and/or the OSA modified starch according to the present invention and the active agent is used in an amount of 0.1 to 100% by weight, based on the total weight of the final product.

The method of encapsulating an active agent as described above can further comprise a step c) which comprises drying of the emulsion, dispersion and/or the precipitate by removing the solvent therefrom.

The drying step c) is preferably carried out such as spray drying, microwave drying, fluidized bed drying, continuous fluidized bed drying, spray dripping, spray congealing, spray chilling, tray drying, drum drying, belt drying and/or freeze drying and/or extrusion, all with or without solvent recoverage.

In a preferred embodiment the OSA modified starch according to the present invention is dispersed in water, the active agent can be added and emulsified, dispersed and/or precipitated, and the emulsion, the dispersion and/or the precipitate can be dried, thus forming the encapsulated product. Alternatively the emulsion, dispersion and/or precipitate can be maintained in a liquid more or less concentrated form, e.g as a color emulsion concentrate or flavor beverage emulsion concentrate or similar.

Thereby, various additives, like pH-regulators, preservatives, antioxidants, sugars, granular native or gelatinized starches or modified starches, dextrins, such as maltodextrin, solvents, such as glycerin or glycerol, coloring agents, hydrocolloidal gums, such as gum *arabicum*, gum acacia or guar and/or flavoring agents can be added.

The dried encapsulating material according to the present invention is further preferably characterized in that the positive properties of the emulsions, the dispersions and/or the precipitates, like small and stable particle sizes are preserved, even if the emulsions, dispersions and/or the precipitates are reconstituted.

The resultant OSA modified starch according to the present invention or an active agent encapsulated in the OSA modified starch according to the present invention can be used in various food products including, but not limited to, cereals, powdered or liquid drink mixes and beverage emulsions, such as soft drinks, vitamin drinks or sport drinks, instant coffees and teas, food supplements, dietary supplements, powdered sauce and gravy mixes, instant soups, powdered dressings, bakery products, flavors, fragrances, colorants, and other dry, solid and/or semi-solid food products for the nutrition of humans and animals. Upon preparation of these powdered and instant products, moisture triggers the release mechanism, providing the active agent to the consumer.

Further, the OSA modified starch according to the present invention or an active agent encapsulated in the OSA modified starch according to the present invention can be used in personal care products including antiperspirants, deodorants, soaps, fragrances, and cosmetics, hair care products, such as hair sprays, mousses, shampoos, cream rinses, and gels, paper products such as diapers, sanitary napkins, paper towels, tissues, toilet tissues, animal care products such as kitty litter, and household products such as carpet cleaners, and air fresheners.

Moreover, the OSA modified starch according to the present invention or an active agent encapsulated in the OSA modified starch according to the present invention can be used in the area of agricultural industry for the preparation of e.g. herbicides, pesticides and fertilizers.

The resultant OSA modified starch according to the present invention or an active agent encapsulated in the OSA modified starch according to the present invention may also be used in a variety of pharmaceuticals and food supplements for humans and animals, including vitamins, carotenoids and mineral nutrients.

Further, the OSA modified starch according to the present invention or an active agent encapsulated in the OSA modified starch according to the present invention can be used in a pharmaceutical dosage form, such as tablets, hard and soft capsules, powders, granulates, or pellets, as well as soft or semisolid formulations. The OSA modified starch according to the present invention or an active agent encapsulated in the OSA modified starch according to the present invention allows for good compressibility and hardness of the tablet as well as a minimized loss of active agent during and after compression or capsule filling. Further, it may allow for high load and retention of a variety of active agents as well as oxidative resistance. Additionally, the pharmaceutical products comprising the OSA modified starch according to the present invention or an active agent encapsulated in the OSA modified starch according to the present invention have an optimized release and bioavailability of the respective active agent.

Compressed tablets are also well-known, particularly in the pharmaceutical industry. Known methods of tableting include direct compression, dry compaction and wet or dry granulation followed by compression. Tablet formulations characteristically should be free flowing, cohesive and lubricating. Sometimes, it is desired to encapsulate a component of the tablet.

The encapsulated product may generally be used at the desired level, the amount being dependent upon the amount of active agent to be incorporated, the desired hardness of the tablet, and the oxidative resistance desired. In general, the encapsulated product will be used in an amount of from about 0.1 to about 99% by weight of the tablet allowing for the active agent to be incorporated in an amount of from about 0.1 to about 60%, particularly from about 10 to about 50%, by weight of the tablet.

The encapsulated product is particularly useful in a compressed tablet or pellet form. The compressed tablet may be made using any method known in the art, particularly by direct compression of the tablet components. In the alternative, the tablet may be prepared by dry blending the encapsulated product with the other components of the formulation, granulating the mixture such as by fluid bed technology, roller compactor, extrusion, or high shear granulator, and dry compacting to a tablet.

Pharmaceutical excipients known in the art may be added to the pharmaceutical dosage form to impart satisfactory processing, compression, and disintegration characteristics to the formulation. Such excipients include, but are not limited to, diluents, flow enhancer, binders, lubricants and glidants, disintegrants, colors, flavors and sweetening agents. These excipients are well known in the art and are limited only by compatibility and characteristics desired.

Binders for the present invention include native and pregelatinized starches, gelatin, microcrystalline cellulose, sugars, carboxymethyl cellulose, methyl cellulose, polyvinyl pyrrolidone, acacia, alginic acid, guar gum, hydroxypropyl methylcellulose, polyethylene glycol and ethylcellulose.

Lubricants and glidants include talc, magnesium stearate, calcium stearate, stearic acid, glyceryl behenate, mineral oil, polyethylene glycol, sodium stearyl fumarate, stearic acid, vegetable oil, zinc stearate, and silicon dioxide.

Disintegrants suitable for the present invention include starches, alginates, gums, croscarmellose, crospovidone, sodium starch glycolate, sodium lauryl sulfate, microcrystalline cellulose, polyacrylates such as polacrilin potassium, and methylcellulose.

Diluents and fillers, respectively suitable for the present invention include dicalcium phosphate, calcium sulfate, lactose, cellulose, Kaolin, mannitol, sodium chloride, starch, sugars, calcium carbonate, calcium phosphate, dextranes, dextrin, malto-dextrins, dextrose, fructose, sorbitol, sucrose, and microcrystalline cellulose.

In particular, a binder is added to the tablet formulation to provide a tablet with desired hardness and low friability. In general the hardness of the resultant tablet is at least about 3, more particularly at least about 4, most particularly at least about 6 kilopascals (kPa). In general, the friability of the resultant tablet is preferably less than 1%, more preferably less than 0.4% of the tablet mass.

Upon contact with water, the moisture triggers the release mechanism, allowing the active agent to be released from the encapsulating starch according to the present invention. For example, upon digestion of the pharmaceutical dosage forms, the active agent is released to the body, wherein a high degree of the dispersion can accelerate the dissolution rate in-vivo, which can lead to an improved absorption and optimum bioavailability.

If the desired final product is other than a pharmaceutical dosage form, alternative additives known to those in the art may be present. For example, flavors and fragrances in a bath oil tablet or surfactants in a detergent tablet.

The encapsulating agent according to the present invention, respectively emulsions, dispersions and/or precipitates containing the OSA modified starch according to the invention have the advantage that they exhibit a relatively small particle size. This small particle size has the advantage of less coalescens, higher color intensity and stability, lower surface oil, better oxidation stability of the encapsulated actives and possibly a better bioavailability particularly at poorly soluble and poorly bioavailable actives and less creaming in liquid formulations.

A small particle size as used herein is a particle size (D90) of less than about 2 µm, preferably less than about 1 µm, and more preferably less than about 0.5 µm. D90 diameter is the diameter at which 90% of a sample's mass is comprised of smaller particles.

Further, the encapsulating agent according to the present invention, respectively emulsions, dispersions and/or precipitates containing the OSA modified starch according to the present invention, have the advantage that they have a constant and uniform particle size.

A uniform particle size as used herein is a particle size, wherein the standard deviation of the average particle diameter D (4,3) is preferably less than 75% of the value of the average particle diameter D (4,3). The average particle diameter D (4,3) is the volume weighted mean diameter also known as the arithmetic mean size in volume % mode.

A constant particle size as used herein is a particle size, wherein the standard deviation of the average particle diameter D (4,3) does not substantially change during the processing and the subsequent storage. In particular it is preferred that the particle size does not change more than about 20%, preferably not more than 10% during the processing and the subsequent storage, preferably at a temperature of about 65° C. in a waterbath for up to 24 h.

The present invention shows that the OSA modified starch according to the present invention has improved emulsifying and dispersing properties and significantly improved emulsion, dispersion and/or precipitate stabilities, which causes better colloidal stabilizing and/or protection properties thus functioning as a protective colloid, when lipophilic phases are stabilized in a hydrophilic environment as a stable matrix.

Thus, the OSA modified starch according to the present invention is functioning as an emulsion and/or dispersion stabilizing starch, which is especially suitable for microencapsulating of active agents and therein superior to starches known in the art.

As mentioned before, the use of the OSA modified starch according to the present invention leads to more improved, especially stable products in the area of emulsions, dispersions and/or precipitates. Further, a colloidal stabilization and/or protection can be achieved more efficiently and with greater stability, and can also be produced more efficiently with greater stability. These improved colloidal stabilizing and/or protection properties at interphases, like oil/water, water/oil, during the formation of emulsions, dispersion and/or precipitates in colloidal, amorphous or fine crystalline form including micro- and nano-emulsions and/or precipitates such as micro and nano-dispersions and micro- and nano precipitates, respectively, as well as multiple emulsions, dispersions and/or precipitates, are a particular advantage of the present invention.

All properties and beneficial effects described above relate to octenyl succinic acid modified starches (OSA modified starches) and methods for producing said octenyl succinic acid modified starches.

However, the present invention also relates to succinic acid modified starches in general. Such succinic acid modified starches generally exhibit the properties and beneficial effects as described above for the OSA modified starches.

As a matter of course, all method steps and methods of measuring have to be adapted accordingly, as known to the person skilled in the art, when a succinic acid modified starch other that octenyl succinic acid modified starch is used.

The term succinic acid modified starch comprises all starches of a natural or a synthetic source that have been derivatized with a succinic acid or a succinic acid derivative. Particular suitable succinic acids comprise succinic acids according to general formula I,

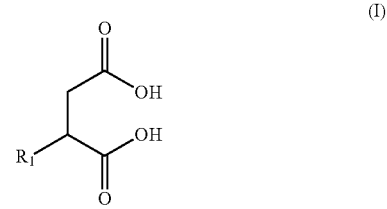

(I)

wherein $R_1$ is an organic substituent comprising a carbon chain with a chain-length of 5 to 22 carbon atoms, preferably with a length of 8, 10, 12, 14 or 16 carbon atoms, more preferably with 8 or 12 carbon atoms, most preferably with 8 carbon atoms.

The term organic substituent comprises alkyl, alkenyl, alkinyl, aralkyl, aralkenyl or aralkinyl groups that can optionally be further substituted.

Most preferably, the succinic acid derivative is oct-1-en-1-yl-succinic acid or dodec-1-en-1-yl-succinic acid.

EXAMPLES

The following examples are presented to further illustrate and explain the present invention and should not be taken as limiting in any regard.

The OSA modified starches used as starting products in the Example can be characterized as follows:

|  | Degradation of the starch | Funnel viscosity [sec] |
|---|---|---|
| OSA Starch 1 | enzymatic | 7.5-9.5 at 19.0% solids determined according to method A |
| OSA Starch 2 | enzymatic | 9.0-10.0 at 19.0% solids, determined according to method A |
| OSA Starch 3 | enzymatic | 12.0-22.0 at 19.0% solids, determined according to method A |
| OSA Starch 4 (Comparative Example) | acid catalyzed | 14.0-18.0 at 8.5% solids, determined according to method B |
| OSA Starch 5 (Comparative Example) | acid catalyzed | 16.0-25.0 at 8.5% solids, determined according to method C |
| OSA Starch 6 (Comparative Example) | Acid catalyzed | 28.0-37.0 At 19.0% solids, Determined according to method D |

The viscosities were measured according to the following methods A, B, C or D.

Method A:
Equipment:
1. Stainless steel Stormer cup.
2. Dual scale thermometer.
3. Cooling bath.
4. BF Funnel (obtained from QMAS Lab).
5. Timer or stop watch.
6. Ring stand and ring to hold BF funnel.
7. 100 mL graduated cylinder.
8. Boiling water bath.
9. Magnetic stirrer.
10. General Electric AF 72 silicone anti-foam emulsion.
Procedure:
1. The stainless steel Stormer Cup and thermometer is tared.
2. 38.0 grams (anhydrous basis) of sample (19% solids) are added into the cup.
3. Purified water is added until the total weight of starch and water is 200.0 grams.
4, One drop silicone emulsion is added.
5. The sample is allowed to mix long enough to dissolve any lumps.
6. The sample solution is heated or cooled to about 22.2° C. (72° F.).
7. 100 mL of the sample solution is run through BF funnel @ 22.2° C. (72° F.) and the flow time for 100 mL is recorded.

Method B:
Equipment:
1. Stainless steel beaker, 600 mL.
2. Thermometer, general purpose, capable of accurately measuring 22.2° C. (72° F.).
3. Cool and/or warm water bath (as required), used to adjust the test sample to 22.2° C. (72° F.).
4. ABF funnel, calibrated, obtained from QMAS Lab.
5. Support stand and 3"-3½" ring, used to hold ABF funnel.
6. Extension clamp, round jaws, used to hold graduated cylinder in an inverted position above funnel.
7. Graduated cylinder, 100 mL.
8. Magnetic stir plate and ~1½"-2" stir bar.
9. Balance, top loading, capable of 0.01 gram accuracy.
10. Weighing boat or smooth surface weighing paper.
11. Magnetic stir bar retriever.
12. Laboratory Film—Parafilm.
13. Stopwatch or timer.
Reagents:
1. pH 6.0 buffer solution:
Preparation of 1 kilogram of pH 6.0 Buffer Solution: 7.74 grams of citric acid, monohydrate and 17.93 grams of sodium phosphate, dibasic, anhydrous are dissolved in 974.33 grams of distilled or deionized water. The suspension is mixed with a magnetic stir bar and stir plate until the citric acid and sodium phosphate have dissolved. The pH of the buffer solution shall be 6.0±0.1. The pH 6.0 buffer solution is transferred from the beaker into a clean, dry container.
Procedure:
1. 17.0±0.05 grams (anhydrous basis) of sample are weighed on an appropriate size weighing paper.
2. The stainless steel beaker is tared.
3. The necessary amount of pH 6.0 buffer solution for a total charge (starch+buffer solution) of 200.0 grams is weighed into the beaker (Weight of pH 6.0 buffer solution is calculated as 200.0—weight of 'as is' starch).
4. A magnetic stir bar is added and the beaker is placed on a magnetic stirrer before mixing is started.
5. While mixing, the pre-weighed starch sample is slowly added into the beaker. The speed of the mixer is adjusted to obtain a good vortex.
6. After addition of all starch, the beaker and its contents are weighed, and recorded for the "total weight".
7. The beaker is covered with parafilm and mixing is continued until the sample is fully dispersed.
8. After the sample is fully dispersed, the sample is taken off the stir plate and the parafilm is removed.
9. The sample is adjusted for moisture loss by adding purified water, to bring the sample to the "total weight" recorded in step #6, and mixed again to obtain a homogenous sample.
10. The stir bar is removed.
11. A support stand with ring and extension clamp is set up so that the top of the ABF funnel is 12" above the base of the support stand when placed in a 3" to 3½" ring. The extension clamp should be set so that the cylinder mouth is 2"-2½" above the top of the funnel when hung inverted in the extension clamp.
12. The sample is heated or cooled to 22.2° C.±0.3° C. (72° F.±1° F.) in a warm or cool water bath. The sample is stirred to temperature using the thermometer.
13. 100 mL of the sample are transferred to a graduated cylinder.
14. The contents of the cylinder is poured into the funnel while holding a finger over the tip orifice. The air is removed from the funnel stem and tip by allowing a small amount of sample to run through the tip back into the graduated cylinder. This small amount of sample is poured back to the funnel, the cylinder is hung upside down in the extension clamp, and allowed to drain into the funnel.

15. Using a stopwatch or timer, the time for the 100 mL of 22.2° C.±0.3° C. (72° F.±1° F.) solution to flow through the funnel back into the beaker is recorded. The time is measured din seconds until the sample flows to the apex of the stem.

Method C:

Equipment:

1. Stainless steel Stormer cup, 300 mL capacity.
2. Thermometer, general purpose, capable of accurately measuring 22.2° C. (72° F.).
3. Cooling bath or warm water bath, used to adjust the test sample to 22.2° C. (72° F.).
4. ABF funnel, calibrated (obtained from QMAS Lab).
5. Support stand and 3"-3½" ring (used to hold ABF funnel).
6. Extension clamp, round jaws, used to hold graduated cylinder in an inverted position above funnel.
7. Graduated cylinder, 100 mL.
8. Magnetic stir plate and ~1½"-2" stir bar.
9. Balance, top loading, capable of 0.01 gram accuracy.
10. Magnetic stir bar retriever.
11. Stopwatch or timer.

Procedure:

1. A support stand with ring and extension clamp is set up so that the top of the ABF funnel is 12" above the base of the support stand when placed in a 3" to 3½" ring. The extension clamp should be set so that the cylinder mouth is 2"-2½" above the top of the funnel when hung inverted in the extension clamp.
2. The moisture content of the sample being tested is determined.
3. A stainless steel Stormer cup is tared.
4. 25.5 grams (anhydrous basis) of sample is added into the cup.
5. Purified water is added until the total weight of starch and water is 300.0 grams.
6. A magnetic stir bar iss added and placed on a magnetic stirrer. The sample is mixed until thoroughly dispersed.
7. The stir bar is removed.
8. The sample is heated or cooled to 22.2° C. (72° F.) using a thermometer to gently stir the sample to temperature.
9, 100 mL of solution is transferred to a graduated cylinder.
10. The contents of the cylinder are poured into the funnel while holding a finger over the tip orifice. The air is removed from the funnel stem and tip by allowing a small amount to run through the tip back into the graduate. This is returned back to the funnel and the cylinder is hung upside down in the extension clamp, allowing it to drain into the funnel.
11. A stopwatch or timer is used to record the time for the 100 mL of 22.2° C. (72° F.) solution to flow through the funnel back into the stainless steel cup. The time is measured until the solution flows to the apex of the stem.

Method D:

Equipment:

1. Waring two-speed commercial blender equipped with a 1-liter stainless steel container.
2. Variable voltage transformer (Variac), 120/140 volt (Fisher Scientific #09-521-110 or equivalent).
3. Top loading balance capable of 0.01 gram accuracy (Ohaus GT4800 or equivalent).
4. Weighing paper (or equivalent).
5. Small spatula (or equivalent).
6. 1000 ml fat separator (soup skimmer), type for kitchen use, available at retail stores (optional).
7. Beaker, 400 mL stainless steel, or equivalent.
4. Dual scale thermometer.
5. Cooling bath capable of cooling to 22.2° C. (72° F.).
6. BF Funnel, calibrated (obtained from QMAS Laboratory).
7. Electric timer or stop watch.
8. Ring stand, ring and finger clamp to hold the BF funnel and graduated cylinder.
9. 100 mL graduated cylinder.

Procedure:

1. 57.0 grams (anhydrous) of starch are weighed onto weighing paper.
2. The required amount of water is weighed directly into the stainless steel blender container to bring the total charge of starch and water to 300 grams.
3. The blender container is placed onto the blender base and connect the blender to a Variac. With the blender on low speed setting, the Variac is increased until a vortex is formed.
4. Two drops of defoamer are added to the blender container.
5. The starch sample is added rapidly but uniformly to the blender. If necessary, the speed is increased by turning up the Variac to just maintain a vortex. The sides of the blender cup are scraped down with a spatula to incorporate all the starch into the dispersion.
6. The sample is continuously mixed for about 3 to 5 minutes, until all visible particles are dispersed.
7. The contents are transferred to a fat separator or a 400 mL beaker, and the sample is allowed to sit undisturbed for about 30 minutes.
8. After 30 minutes, either the defoamed sample is poured from the fat separator into a 400 mL beaker or any foam that has come to the top of the beaker is removed with a spoon or spatula and discarded.
9. The temperature of the sample is adjusted to 22.2+/−0.3° C. (72+/−0.5° F.).
10. 100 mL of the mixture is transferred from the beaker to a 100 mL graduated cylinder and:

a) A finger is placed over the orifice of the BF funnel. 100 mL is poured into the funnel.

The finger is removed slightly allowing some of the mixture back into the graduate, clearing the stem of any foam or trapped air. The graduate is placed in an inverted position above the funnel, allowing it to drain while the test sample flows through the funnel back into the beaker.

b) The stopwatch is started and the finger simultaneously removed. The watch is stopped when the liquid surface (not foam) reaches the apex of the funnel (where the stem begins). The time is recorded in seconds.

The OSA modified starches according to the present invention were prepared as follows:

In each case of the OSA modified, enzymatically degraded starches (OSA Starches 1 to 3) as well as of acid hydrolyzed starches (OSA Starches 4 to 6) as comparative examples (all purchased from Ingredion), about 0.5 to 1 kg was weighed in a tray.

Subsequently, each starch was tempered in the tray in a Memmert drying cabinet (Memmert GmbH & Co KG) for the specified time and the specified temperature. The air pressure was not modified during drying.

During tempering, the OSA modified starches were mixed and stirred about every 30 min to prevent clumping and clogging.

After tempering the tempered starch was sieved through a conventional household sieve to remove bigger clumps.

Example 1: Analysis of the OSA Modified Starches According to the Present Invention A) Analysis of Non-Covalently Bound, Free Octenyl Succinic Acid and of the covalently Bound Octenyl Succinic Acid in the OSA Modified Starches Prior and after the Tempering.

The portion of non-covalently bound, free octenyl succinic acid is determined as follows by HPLC.

Sample Preparation for Determining the Content of Non-Covalently Bound, Free Octenyl Succinic Acid:

In each case 125 mg of the OSA modified starch is weighed into a 20 mL vial, to which is added 15.0 mL of methanol. The vial is sealed and mixed for 18 h. the sample is diluted with water to yield a 2:1 water:methanol solution. The solution is filtered through a PVDF 0.45 µm filter and analyzed Sample Preparation for Determining the Total Content of Octenyl Succinic Acid:

In each case 20 mg starch is weighed into a 20 mL vial, to which is added 15.0 mL 0.05N KOH solution. The vial is crimp capped and heated at 75° C. for 3 h or until the starch is completely dissolved. The sample is allowed to cool, filtered through a filter, and collected for analysis.

Preparation of a Standard/Reference Material for the Analysis of the OSA Modified Starches:

In each case 20 mg of reference material, octenyl succinic acid anhydride (CAS No.: 42482-06-4), is weighed into a 20 mL vial to which is added 20 mL 0.1N KOH solution. The reference is heated at 75° C. for 3 h until the octenyl succinic acid anhydride is completely dissolved. Secondary standards are prepared by diluting stock solution using 33/67 methanol/water producing standards in the range of 0.2 to 20 µm/mL OSA.

Analysis was carried out using Empower-HPLC
Mobile phase: Channel A, 1.0% phosphoric acid aqueous solution
Channel B, acetonitrile
Flow Rate: 0.3 mL/min
Column: Cortecs C18 2.7 µm, 2.1×100 mm
Column Temperature: 40° C.
UV Detection Wavelength: 205 nm
Analysis Time: 20 min
Injection Volume: 5.0 µL
Retention time: 5.5 min and 6.0 min The content of covalently bound octenyl succinic acid is calculated as the difference between the total content of octenyl succinic acid and the content of non-covalently bound, free octenyl succinic acid.

The results are given in Table 1.

TABLE 1

Analysis of free and covalently bound octenyl succinic acid (OSA)

| | Degradation of the starch | Tempering | Total OSA (%) | Free OSA (%) | Covalently bound OSA (%) (calculated) |
|---|---|---|---|---|---|
| OSA Starch 1 | enzymatic | — | 2.44 | 0.52 | 1.92 |
| | | 3 h @150° C. | 2.52 | 0.44 | 2.08 |
| OSA Starch 2 | enzymatic | — | 2.50 | 0.69 | 1.80 |
| 2 | | 3 h @150° C. | 2.52 | 0.41 | 2.11 |

TABLE 1-continued

Analysis of free and covalently bound octenyl succinic acid (OSA)

| | Degradation of the starch | Tempering | Total OSA (%) | Free OSA (%) | Covalently bound OSA (%) (calculated) |
|---|---|---|---|---|---|
| OSA Starch 3 | enzymatic | — | 2.60 | 0.75 | 1.85 |
| | | 3 h @150° C. | 2.56 | 0.40 | 2.16 |

Table 1 shows that the content of free octenyl succinic acid can be reduced with tempering.

B) Analysis of Non-Covalently Bound, Free Octenyl Succinic Acid and covalently Bound Octenyl Succinic Acid in the OSA Modified Starches According to the present Invention after Tempering for Different Times.

The samples were prepared and the analysis was performed as described in Example 1A.

The results are given in Table 2.

TABLE 2

Analysis of non-covalently bound, free and covalently bound octenyl succinic acid at different times of tempering.

| | Tempering | Total OSA (%) | Free OSA (%) | Covalently bound OSA (%) (calculated) |
|---|---|---|---|---|
| OSA Starch 1 | 2 h @150° C. | 2.78 | 0.47 | 2.31 |
| OSA Starch 1 | 4 h @150° C. | 2.76 | 0.45 | 2.31 |
| OSA Starch 1 | 6 h @150° C. | 2.79 | 0.42 | 2.37 |
| OSA Starch 1 | 8 h @150° C. | 2.73 | 0.10 | 2.63 |
| OSA Starch 2 | 2 h @150° C. | 2.80 | 0.44 | 2.36 |
| OSA Starch 2 | 4 h @150° C. | 2.81 | 0.39 | 2.42 |
| OSA Starch 2 | 6 h @150° C. | 2.79 | 0.36 | 2.40 |
| OSA Starch 2 | 8 h @150° C. | 2.74 | 0.17 | 2.57 |

The results in Table 2 show that tempering reduces over time the content of non-covalently bound, free octenyl succinic acid. Yet, the viscosity of the starches increases if tempered for more than 6 h so that the emulsions and/or dispersions of the starches need to be diluted, because they need to be dried with a lower dry solids content.

C) Analysis of the DE-Values

The dextrose equivalent was determined by the titration method for total sugars #-10-9070 under the NF 22 monograph far noncrystallizing sorbitol solution. In duplicate 0.05 or 0.10 g starch was accurately weighed into an Erlenmeyer flask and brought to a weight of 50 g with deionized water, to which was added 50 mL cupric sulfate iodide. The solution was gently refluxed on a hot plate for 5 min and then cooled to room temperature. Thereafter 25 mL 5N sulfuric acid was added slowly with constant stirring. The solution was then titrated with 0.1N sodium thiosulfate and starch indicator to reach a sky blue equivalent point. Reducing sugar (%) was calculated by subtracting the volume of titrant in the blank form from the volume of titrant in the sample, converting the mL titrant into mg of sugar from the #5-10-9070 reference table, and dividing the mg sugar by 10 times the grams of sample used.

The results are shown in Table 3.

TABLE 3

| | DE values | |
|---|---|---|
| | Tempering | DE-value |
| OSA Starch 1 | — | 36.5 |
| | 3 h @150° C. | 35.3 |

D) Analysis of the Content of Alpha-1,6-Glycosidic Linkages

The content of alpha-1,6-glycosidic linkages is determined using high-temperature $^1$H-NMR.

The solid samples were dissolved in $D_2O/TSP-d_4$ on a steam bath and $^1$H-NMR spectra were measured at 90° C. using a Bruker Avance III HD 400 MHz NMR instrument at 400 MHz, TSP-$d_4$ was added as internal standard.

The results are shown in Tables 4 and 5.

TABLE 4

| | Alpha-1,6-glycosidic linkages | | |
|---|---|---|---|
| | Degradation of the starch | Temerping | alpha-1,6-glycosidic linkages (%) |
| OSA Starch 1 | enzymatic | — | 11.4 |
| | | 3 h @150° C. | 13.1 |
| OSA Starch 2 | enzymatic | — | 11.0 |
| | | 3 h @150° C. | 13.3 |
| OSA Starch 3 | enzymatic | — | 10.6 |
| | | 3 h @150° C. | 13.9 |
| OSA Starch 4 (comparative example) | acid catalyzed | — | 5.1 |
| | | 3 h @150° C. | 4.6 |
| OSA Starch 6 (comparative example) | acid catalyzed | 3 h @150° C. | 5.9 |
| OSA Starch 5 (comparative example) | acid catalyzed | — | 4.8 |
| | | 3 h @150° C. | 5.6 |

TABLE 5

| Alpha-1,6-glycosidic linkages at different time points during tempering | | |
|---|---|---|
| | Tempering | alpha-1,6-glycosidic linkages (%) |
| OSA Starch 1 | — | 11.4 |
| OSA Starch 1 | 2 h @150° C. | 12.8 |
| OSA Starch 1 | 4 h @150° C. | 15.6 |
| OSA Starch 1 | 6 h @150° C. | 16.6 |
| OSA Starch 1 | 8 h @150° C. | 18.7 |
| OSA Starch 2 | — | 11.0 |
| OSA Starch 2 | 2 h @150° C. | 12.2 |
| OSA Starch 2 | 4 h @150° C. | 14.2 |
| OSA Starch 2 | 6 h @150° C. | 14.7 |
| OSA Starch 2 | 8 h @150° C. | 17.5 |

The enzymatically degraded starches naturally have a higher content of alpha-1,6-glycosidic linkages, which can be increased during tempering. Yet, the viscosity of the starches increases if tempered for more than 6 h so that the emulsions and/or dispersions of the starches need to be diluted, because they need to be dried with a lower dry solids content.

E) Analysis of the Surface Tension of a Solution Comprising the OSA Modified Starch According to the Present Invention Samples of the starch were suspended in water and stirred over-night with a magnetic stirrer. On the day of measurement, further dilutions of the stock solution were prepared and the surface tension was determined with a Kruess-tensiometer K11 MK3 using the plate method at 20° C. Values were recorded every 60 s for 10 min. Samples were measured up to four times. Differences between the samples were analyzed with a single factor variance with post-hoc test according to Fisher. Missing values were extrapolated for evaluation.

The results are shown in Table 6.

TABLE 6

| Surface tension of solutions comprising the OSA modified starches | | | | | | | | |
|---|---|---|---|---|---|---|---|---|
| | OSA Starch 1 | | OSA Starch 2 | | OSA Starch 1 | | OSA Starch 2 | |
| | | | | | Tempering | | | |
| Concentration | — | | — | | 3 h @150° C. | | 3 h @150° C. | |
| 0.10% | 58.97 | ±1.27 | 57.15 | ±1.63 | 43.45 | ±2.76 | 42.40 | — |
| 0.25% | 52.05 | ±1.11 | 50.95 | ±0.64 | 39.20 | — | 36.35 | ±1.20 |
| 0.50% | 43.07 | ±2.63 | 46.17 | ±3.27 | 34.50 | ±0.42 | 35.40 | ±0.85 |
| 0.75% | 43.35 | ±0.78 | 43.30 | — | 35.18 | ±0.47 | 35.50 | ±1.40 |
| 1.00% | 43.13 | ±1.46 | 38.90 | ±2.43 | 34.40 | ±0.38 | 33.95 | ±2.62 |
| 2.00% | 39.15 | ±1.91 | 36.85 | ±0.21 | — | — | 33.10 | — |
| 3.00% | 37.45 | ±0.21 | 30.80 | ±1.84 | 31.80 | ±0.68 | 30.85 | ±1.06 |

Analysis of the surface tensions shows that solutions containing the OSA modified starch according to the present invention have a reduced surface tension, which leads to a better emulsifying activity as well as a better wetting behavior and accordingly to an optimized colloidal protection and/or stabilizing activity as well as dispersion stabilizing activity.

F) Analysis of the pH of a 5% by Weight Aqueous Solution Comprising the OSA Modified Starches Prior and after Tempering The results are shown in Table 7.

TABLE 7 pH-values

|  | Tempering | pH (5% by weight modified starch in water) |
|---|---|---|
| OSA Starch 1 | — | 4.23 |
|  | 3 h @150° C. | 4.23 |
| OSA Starch 2 | — | 4.18 |
|  | 3 h @150° C. | 4.18 |
| OSA Starch 3 | — | 4.21 |
|  | 3 h @150° C. | 4.15 |
| OSA Starch 5 (comparative example) | — | 4.21 |
|  | 3 h @150° C. | 4.15 |

Tempering does not substantially influence the pH of an aqueous solution measured at ambient temperatures (15° C. to 25° C.) comprising 5% by weight of the OSA modified starches.

G) Analysis of the Molecular Weight of the Starch Portion of the OSA Modified Starches Prior and after the Tempering The OSA modified starch was dissolved in DMSO overnight and subsequently heated at about 95 to 100° C. for 1 h followed by cooling of the solution.

The obtained solution was filtered through a 0.45 μm PP membrane and the molecular weight was determined by gel permeation chromatography using the following parameters.
Column set: Phenogel™ 10 μm 100 Å, $10^3$ Å, $10^5$ Å
Guard column: Phenogel™ 10 μm
Injection volume: 100 10 μL
Number of Injections: 2/sample
Standards: Pullulan (788 K-180 Da)
Sample concentration: 10.3-10.8 mg/4 mL
Detector: RID-10A from Shimadzu
Column Temperature: 60° C.
Mobile-phase: DMSO+0.03 M $NaNO_3$
Flow rate: 1 mL/min
Run time: 45 min The results are shown in Table 8.

TABLE 8

Molecular weight

|  | Tempering | $M_w$ [Da] starch portion | $M_n$ [Da] starch portion | $M_w$ [Da] low MW portion | $M_n$ [Da] low MW portion |
|---|---|---|---|---|---|
| OSA Starch 1 | — | 90554 | 16278 | 451 | 364 |
|  | 3 h @150° C. | 114480 | 18899 | 558 | 397 |
| OSA Starch 2 | — | 152318 | 20938 | 452 | 363 |
|  | 3 h @150° C. | 211872 | 24783 | 598 | 407 |
| OSA Starch 5 (comparative example) | — | 2087236 | 107922 | — | — |
|  | 3 h @150° C. | 207371 | 15485 | — | — |

($M_w$: mass average of the molar mass; $M_n$: number average of the molar mass)

The molecular weight of the OSA modified starches according to the present invention increases during tempering. The molecular weight of OSA modified starches not according to the present invention decreases during tempering.

H) Analysis of Viscosities of Solutions of OSA Modified Starches Before and after Tempering

TABLE 9

Analysis of viscosities

|  | Tempering | Viscosity [MPas] of a 28.57% by weight aqueous solution of the OSA modified starch | Viscosity [MPas] of a 15% by weight aqueous solution of the OSA modified starch |
|---|---|---|---|
| OSA Starch 1 | — | 54 | — |
|  | 2 h @150° C. | 62 | — |
|  | 3 h @150° C. | 62 | — |
|  | 4 h @150° C. | 65 | — |
|  | 6 h @150° C. | 75 | — |
| OSA Starch 2 | — | 74 | — |
|  | 3 h @150° C. | 94 | — |
| OSA Starch 5 (comparative example) | — | — | 246 |
|  | 3 h @150° C. | — | 46 |

The viscosity was measured on a Brookfield RV viscometer with spindle 3 at 100 rpm at 20° C.

The viscosity of an aqueous solution of the OSA modified starch according to the invention increases with the tempering. The viscosity of an aqueous solution of an OSA modified starch not according to the invention (OSA Starch 5's degradation is catalyzed by an acid) decreases with the tempering.

I) Analysis of the C.I.E.-LAB Color Values of the OSA Modified Starch Before and after Tempering

TABELLE 10

C.I.E-LAB-Farbwerte

|  | Tempering | L-value | a-value | b-value |
|---|---|---|---|---|
| Hi-Cap 100 L | — | 96.3 | −0.2 | 2.1 |
| Hi-CAP 100 L | 2 h @150° C. | 89.4 | 0.4 | 12.9 |
| Hi-CAP 100 L | 3 h @150° C. | 84.2 | 1.9 | 16.6 |
| Hi-CAP 100 L | 4 h @150° C. | 79.3 | 3.4 | 20.5 |
| Hi-CAP 100 L | 5 h @150° C. | 74.3 | 5.2 | 22.0 |
| Hi-CAP 100 L | 6 h @150° C. | 68.0 | 7.8 | 22.5 |
| Hi-CAP 100 H | — | 95.8 | −0.3 | 2.4 |
| Hi-CAP 100 H | 2 h @150° C. | 84.4 | 1.8 | 15.9 |
| Hi-CAP 100 H | 3 h @150° C. | 79.8 | 3.5 | 18.7 |
| Hi-CAP 100 H | 4 h @150° C. | 74.2 | 5 | 21.1 |
| Hi-CAP 100 H | 6 h @150° C. | 72.1 | 5.9 | 21.7 |
| Hi-CAP 100 H | 8 h @150° C. | 61.9 | 9.3 | 21.4 |

The L-value gives the brightness, the α-value gives the red-green content and the b-value gives the yellow-blue content of a color. The L-values are generally positive and lie between 0 for ideal black colors and 100 for ideal white colors.

Example 2: Analysis of the OSA Modified Starches According to the Present Invention in an Emulsion Comparison of tempered (according to the invention) and not tempered (not according to the invention) enzymatically degraded OSA Starch 1 or 1and a comparative starch that was degraded under acid catalysis as emulsifier in an oil/water emulsion.

An oil in water emulsion was prepared with different OSA modified starches as follows.

59.75% by weight water, 0.2% by weight citric acid and 0.05% by weight sodium benzoate, were added to a flask and mixed with a propeller stirrer until all ingredients were dissolved. Then 24% by weight starch were added. To this solution 16.0% by weight Delios V Oil (MCI Oil purchased from BASF) were added and the solution was further stirred for 3 min at 20° C.

Subsequently, the emulsion was tested for its thermostability. Samples were incubated in a water bath at 65° C. for 1 h, 3 h and 1 d, before the average particle diameter was determined. Additionally, the viscosities of the emulsions were determined.

The average particle diameter vias measured on a "Light scattering particle size analyzer", LS 13320, Beckman Coulter.

Viscosities were measured on a Brookfield RV viscometer with spindle 3 at 100 rpm at 20° C.

Results are shown in Tables 11, 12 and 13.

TABLE 11

Viscosities and particle diameter d(90) after incubation of the oil in water emulsions comprising OSA modified starches for 1 h, 3 h and 1 d, at 20° C. or 65° C.

| | OSA Starch 1 | OSA Starch 1 | OSA Starch 5 (comparative example) | OSA Starch 5 (comparative example) |
|---|---|---|---|---|
| Tempering | — | 3 h @150° C. | — | 3 h @150° C. |
| Viscosity after 1 d @20° C. [mPas] | 102 | 143 | 558 | 64 |
| Viscosity after 1 d @65° C. [mPas] | 46 | 59 | 182 | 30 |
| D90 [μm] fresh | 0.81 | 0.51 | 1.25 | 1.40 |
| D90 [μm] after 1 d @20° C. | 0.82 | 0.51 | 1.31 | 1.38 |
| D90 [μm] after 1 h @65° C. | 20.6 | 0.51 | 1.28 | 1.39 |
| D90 [μm] after 3 h @65° C. | 2.85 | 0.51 | 1.32 | 1.38 |
| D90 [μm] after 1 d @65° C. | 4.63 | 0.51 | 1.29 | 1.38 |

TABLE 12

Particle diameter D(4, 3) after incubation of the oil in water emulsion comprising OSA modified starches for 1 h, 3 h and 1 d, at 65° C.

| | Tempering | Average D(4, 3) particle diameter | Standard deviation |
|---|---|---|---|
| OSA Starch 1 Fresh emulsion | — | 0.506 | 0.269 |
| OSA Starch 1 after 1 h @65° C. | — | 0.944 | 0.924 |
| OSA Starch 1 after 3 h @65° C. | — | 1.280 | 1.240 |
| OSA Starch 1 after 1 d @65° C. | — | 2.140 | 1.730 |
| OSA Starch 1 Fresh emulsion | 3 h @150° C. | 0.322 | 0.151 |
| OSA Starch 1 after 1 h @65° C. | 3 h @150° C. | 0.322 | 0.150 |
| OSA Starch 1 after 3 h @65° C. | 3 h @150° C. | 0.333 | 0.148 |
| OSA Starch 1 after 1 d @65° C. | 3 h @150° C. | 0.410 | 0.148 |

The OSA modified starches that were tempered for 3 h at 150° C. and are thus according to the present invention, have a significantly smaller and more constant particle size in the emulsion compared to starches that were not tempered and are thus not according to the invention. Also a starch not according to the invention because it was degraded under acid catalysis (OSA Starch 5) does not show these small particle sizes.

Further, the standard deviation of the average particle diameter D (4,3) is much smaller for the emulsions comprising the OSA modified starches according to the present invention.

FIG. 1 shows the particle diameter distribution for the tempered OSA Starch 1, and FIG. 2 for the not tempered OSA Starch 1. FIG. 3 shows the particle diameter distribution for the tempered OSA Starch 5 and FIG. 4 for the not tempered OSA Starch 5 (FIGS. 3 and 4 are comparative examples).

A comparison of the data presented in these Figures show a significantly uniform, sharper, particle diameter distribution which is further more stable for the OSA modified starch based emulsions according to the present invention (OSA Starch 1), also when incubated at higher temperatures over a longer period of time.

TABLE 13

Viscosities of aqueous starch/oil emulsions

| | Concentration starch/oil in the emulsion | Tempering | Viscosity at 20° C. [mPas] | Viscosity at 65° C. [mPas] |
|---|---|---|---|---|
| OSA Starch 1 | 24%/16% | — | 102 | 46 |
| OSA Starch 1 | 24%/16% | 2 h @150° C. | 120 | 52 |
| OSA Starch 1 | 24%/16% | 3 h @150° C. | 142 | 62 |
| OSA Starch 1 | 24%/16% | 4 h @150° C. | 168 | 64 |
| OSA Starch 1 | 24%/16% | 6 h @150° C. | 235 | 68 |
| OSA Starch 1 | 16.8%/11.2% | 8 h @150° C. | 452 | 75 |
| OSA Starch 2 | 24%/16% | — | 272 | 76 |
| OSA Starch 2 | 24%/16% | 3 h @150° C. | 572 | 120 |

Viscosities were determined on a Brookfield RV viscometer with spindle 3 at 100 rpm at 20° C. and 65° C., respectively. The viscosities of the emulsions increase with increasing tempering time.

Example 3: Analysis of the OSA Modified Starches as Encapsulating Agents

An emulsion consisting of 60% by weight demineralized water, 31.86% by weight OSA Starch 1, 0.14% by weight ascorbic acid, 5.03% by weight Delios MCT Oil (BASF), 2.67% by weight of a 30% natural beta-carotene dispersion and 0.3% by weight alpha-tocopherol was prepared as described in Example 2, wherein the beta-carotene was dispersed and dissolved in the oil phase. The emulsion was then incubated in a water bath as described in Example 2.

Moreover, a sample of the emulsion was spray-dried after incubation for 1 d at 65° C. and reconstituted in water.

The spray-drying was performed in a Büchl B290 lab spray-dryer using the following settings
Inlet temperature; 180° C.
Outlet temperature: 80-90° C.
Temperature of the emulsion: 50-60° C.
Pump speed: 60-65%
Aspirator: 80-85%
Air pressure: 12 bar
Air flow rate: 45%

All particle diameters were determined as described for Example 2. The results are shown in Tables 14 and 15.

TABLE 14

Particle diameters (D90)

| | OSA Starch 1 + β-carotene | OSA Starch 1 + β-carotene |
|---|---|---|
| Tempering | — | 3 h @150° C. |
| D90 [μm] frisch | 0.57 | 0.36 |
| D90 [μm] nach 1 d @20° C. | 0.59 | 0.36 |
| D90 [μm] nach 1 h @65° C. | 0.63 | 0.38 |
| D90 [μm] after 3 h @65° C. | 1.03 | 0.41 |
| D90 [μm] after 6 h @65° C. | 1.23 | 0.39 |
| D90 [μm] after 1 d @65° C. | 2.03 | 0.38 |
| D90 [μm] after reconstitution of the spray-dried powder | 1.28 | 0.38 |

TABLE 15

Particle diameters (D(4, 3))

| | Tempering | Average D(4, 3) particle diameter [μm] | Standard deviation [μm] |
|---|---|---|---|
| OSA Starch 1 + β-carotene fresh emulsion | — | 0.388 | 0.125 |
| OSA Starch 1 + β-carotene after 1 d @65° C. | — | 1.030 | 1.570 |
| OSA Starch 1 + β-carotene after reconstitution of the spray-dried powder | — | 0.591 | 0.453 |
| OSA Starch 1 + β-carotene fresh emulsion | 3 h @150° C. | 0.186 | 0.128 |
| OSA Starch 1 + β-carotene after 1 d @65° C. | 3 h @150° C. | 0.208 | 0.130 |
| OSA Starch 1 + β-carotene after reconstitution of the spray-dried powder | 3 h @150° C. | 0.231 | 0.126 |

The OSA modified starches according to the present invention, which were tempered for 3 ft at 150° C., show a significantly smaller and more uniform particle size in the emulsion compared to starches not tempered. This result was also found for the spray-dried powder after reconstitution.

Further, the standard deviation of the average particle diameter D (4,3) of the OSA modified starches according to the present invention is much smaller.

FIG. 5 shows the particle size distribution for the not tempered OSA Starch 1. FIG. 6 shows the particle size distribution for the tempered OSA Starch 1. With this comparison the more uniform and more stable particle size distribution of the tempered OSA Starch 1 is clearly shown.

FIG. 7 shows the particle size distribution of the not tempered OSA Starch 1+β-carotene after reconstitution, and FIG. 8 shows the particle size distribution of the tempered OSA Starch 1+β-carotene after reconstitution. Also this comparison shows the more uniform and more stable particle size distribution of the tempered OSA Starch 1+β-carotene, even after reconstitution.

Example 3: Analysis of the OSA Modified Starches According to the Present Invention in Comparison with a Mixture of OSA Modified Starches and Free OSA-Maltose Emulsions were prepared as described for Example 2 and the following tests have been carried out.
A) Blend of OSA Starch 1 or 2, which was not Tempered and OSA-Maltose:

In order to study the effect of the addition of OSA-maltose, i.e. partly replacing OSA Starch 1 or 2, which was not tempered with OSA-maltose on the emulsion stability, blends as set forth in Table 16 were prepared and the emulsion test conducted as described above.

5% and 20%, respectively, of the OSA Starch 1 or 2 were replaced by OSA-maltose. The emulsion prepared from these blends were tested at ambient (20° C.) and elevated (65° C.) temperatures and the particle size distribution was investigated as described above. Comparison was made against OSA Starch 1 or 2, which was not tempered and the OSA Starch 1 or 2 which was tempered for 3 hours at 150° C.

TABLE 16

Fineness of emulsion (with added OSA-maltose)-
D90 [μm] of emulsions stored at elevated temperatures

| | 95% OSA Starch 1 not tempered 5% OSA-maltose | 95% OSA Starch 2 not tempered 5% OSA-maltose | 80% OSA Starch 1 not tempered 20% OSA-maltose | 80% OSA Starch 2 not tempered 20% OSA-maltose |
|---|---|---|---|---|
| fresh emulsion | 0.79 | 0.54 | 0.64 | 0.95 |
| 3 h @ 65° C. | 2.85 | 1.69 | 3.26 | 1.80 |
| 1 d @ 65° C. | 4.56 | 3.13 | 4.16 | 2.56 |

FIG. 9 shows the particle size distribution for the mixture of 95% not tempered OSA Starch 1 plus 5% OSA-maltose.

FIG. 10 shows the particle size distribution for the mixture of 95% not tempered OSA Starch 2 plus 5% OSA-maltose, FIG. 11 shows the particle size distribution for the mixture of 80% not tempered OSA Starch 1 plus 20% OSA-maltose.

FIG. 12 shows the particle size distribution for the mixture of 80% not tempered OSA Starch 2 plus 20% OSA-maltose.

There is no effect of OSA-maltose addition to OSA Starch 1 or 2 which is not tempered. Neither 5% nor 20% OSA-maltose addition (blending OSA-maltose with OSA Starch 1 or 2) revealed significant effects on emulsion stability compared with the OSA Starch 1 or 2 which was not tempered alone. Compared with the particle size/emulsions stability improvements of the tempered OSA Starch 1 or 2 respectively, the samples to which OSA-maltose was added show clearly inferior results. For example after 3 hours at 65° C. the D90 of the mixture of 80% not tempered OSA Starch 1 plus 20% OSA-maltose is 3.26, whereas it is 0.51 for tempered OSA Starch 1 according to the invention (see Table 11).
B) Blend of Tempered OSA Starch 2 and OSA-Maltose:

In order to study the effect of replacing 20% OSA Starch 2, which was tempered for 3 hours at 150° C. with OSA-maltose on the emulsion stability, blends as set forth in table 17 were prepared and the emulsion test was conducted as described above. The emulsion was exposed to ambient (20° C.) and elevated (65° C.) temperatures and the particle size distribution was monitored over time as described above.

TABLE 17

| D90 [μm] of emulsions stored at elevated temperatures | | |
|---|---|---|
| | 100% OSA Starch 2 tempered for 3 h@150° C. 0% OSA-maltose | 80% OSA Starch 2 tempered for 3 h@150° C. 20% OSA-maltose |
| fresh emulsion | 0.48 | 0.51 |
| 3 hours @ 65° C. | 0.48 | 0.61 |
| 1 day @ 65° C. | 0.49 | 0.62 |

FIG. 13 shows the particle size distribution of 100% OSA Starch 1 which was tempered for 3 h @150° C.

FIG. 14 shows the particle size distribution for the mixture of 80% OSA Starch 1 which was tempered for 3 h at 150° C. plus 20% OSA-maltose.

There was no positive impact after exchanging 20% of the OSA Starch 1 which was tempered for 3 h at 150° C. by OSA-maltose. The particle size distribution remained as stable as in the reference emulsion.

C) Emulsion Stability of Pure OSA-Maltose

Under the assumption that the used OSA-material had reacted sufficiently with maltose to yield OSA-modified-maltose (OSA-maltose) and to compare its emulsion stabilizing properties as such a further emulsion test with OSA-maltose as sole emulsifier was conducted.

This test is mimicking a typical formulation with 24% OSA Starch 1 or 2 solids that is, 24% solids OSA-maltose was used, to fully replace the OSA modified starch.

TABLE 18

| D90 [μm] of emulsions stored at elevated temperature | | |
|---|---|---|
| | 24% OSA-maltose solids containing 0.72% OSA (added as 40% solution) | 0.72% OSA |
| fresh emulsion | 3.91 | 217.00 |
| 3 hours @65° C. | 149.00 | 208.00 |
| 1 day @ 65° C. | 185.00 | 171.00 |

An emulsion was obtained with a D90 of 3.91 μm. When stored at elevated temperatures of 65° C., however the particle size increased considerably (D90=185 μm), indicating much inferior emulsion stability compared to the emulsions made with OSA Starch 1 or 2 which was not tempered. The considerable increase in oil droplet size upon storage conditions at 65° C. however reveals that OSA-maltose is not suitable for emulsion stabilization at elevated temperatures in general.

A further emulsion produced for comparison made with 0.72% pure OSA (same OSA content as in 24% OSA-maltose containing 3% OSA) revealed that pure OSA is not as effective as the OSA-maltose for emulsion stabilization.

FIG. 15 shows the particle size distribution of 24% OSA-maltose solids containing 0.72% OSA.

FIG. 16 shows the particle size distribution of 0.72% pure OSA.

What is claimed is:

1. An octenyl succinic acid (OSA) modified starch comprising a starch molecule degraded by at least one enzyme capable of cleaving the 1,4-linkages of the starch molecule from the non-reducing ends to produce short chain saccharides, wherein a content of non-covalently bound, free octenyl succinic acid in the OSA modified starch is less than about 0.50% by weight, based on the total weight of the OSA modified starch and wherein a content of an alpha-1, 6-glycosidic linkages is higher than 12% in the OSA modified starch based on the total weight of the OSA modified starch.

2. The OSA modified starch according to claim 1, wherein the OSA modified starch has been degraded to a dextrose equivalent of higher than about 20.

3. The OSA modified starch according to claim 1, wherein the OSA modified starch has been degraded to a dextrose equivalent of about 30 to about 40.

4. The OSA modified starch according to claim 1, wherein a content of a covalently bound octenyl succinic acid in the OSA modified starch is from about 0.1% to 10% by weight, based on the total weight of the OSA modified starch.

5. The OSA modified starch according to claim 1, wherein a content of a covalently bound octenyl succinic acid in the OSA modified starch is from about 0.5% to about 5% by weight, based on the total weight of the OSA modified starch.

6. The OSA modified starch according to claim 1, wherein a content of a covalently bound octenyl succinic acid in the OSA modified starch is from about 2% to about 3% by weight, based on the total weight of the OSA modified starch.

7. The OSA modified starch according to claim 1, wherein the OSA modified starch is an OSA modified waxy starch.

8. The OSA modified starch according to claim 1, wherein the OSA modified starch is an OSA modified waxy corn starch.

9. The OSA modified starch according to claim 1, wherein the enzyme is selected from the group consisting of β-amylase, glucoamylase, pullulanase, maltogenase, exo-alpha-1, 4-glucosidase, exo-1,4-alpha-D-glucan maltotetrahydrolase and exo-1,4-alpha-D-glucan-maltohexahydrolase.

10. The OSA modified starch according to claim 1, wherein the enzyme is β-amylase or glucoamylase.

11. The OSA modified starch according to claim 1, wherein 5% by weight aqueous solution of the OSA modified starch has a pH of less than about 7.

12. The OSA modified starch according to claim 1, wherein a 5% by weight aqueous solution of the OSA modified starch has a pH of less than about 4.7.

13. The OSA modified starch according to claim 1, wherein a 0.5% by weight aqueous solution of the OSA modified starch has a surface tension of less than about 40 mN/m.

14. An encapsulation agent comprising the OSA modified starch according to claim 1.

* * * * *